US011382688B2

(12) United States Patent
Steinke et al.

(10) Patent No.: US 11,382,688 B2
(45) Date of Patent: *Jul. 12, 2022

(54) SELECTABLE ECCENTRIC REMODELING AND/OR ABLATION

(71) Applicant: BOSTON SCIENTIFIC SCIMED, INC., Maple Grove, MN (US)

(72) Inventors: Tom A. Steinke, San Diego, CA (US); Corbett W. Stone, San Diego, CA (US); Stephen O. Ross, Fallbrook, CA (US); Brian S. Kelleher, Ramona, CA (US); Raphael M. Michel, Palo Alto, CA (US); Donald H. Koenig, San Diego, CA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 439 days.

This patent is subject to a terminal disclaimer.

(21) Appl. No.: 16/218,293

(22) Filed: Dec. 12, 2018

(65) Prior Publication Data
US 2019/0117301 A1    Apr. 25, 2019

Related U.S. Application Data

(60) Continuation of application No. 13/831,634, filed on Mar. 15, 2013, now Pat. No. 10,188,457, which is a
(Continued)

(51) Int. Cl.
*A61B 18/14* (2006.01)
*A61B 18/18* (2006.01)
(Continued)

(52) U.S. Cl.
CPC ......... *A61B 18/1492* (2013.01); *A61B 18/18* (2013.01); *A61B 18/1815* (2013.01);
(Continued)

(58) Field of Classification Search
CPC ..... A61B 18/14; A61B 18/1492; A61B 18/18; A61B 18/1815; A61B 2018/0016;
(Continued)

(56) References Cited

U.S. PATENT DOCUMENTS

| 4,660,571 A | 4/1987 | Hess et al. |
| 4,955,377 A | 9/1990 | Lennox et al. |

(Continued)

FOREIGN PATENT DOCUMENTS

| JP | 08112289 A | 5/1996 |
| JP | 2000140118 A | 5/2000 |

(Continued)

OTHER PUBLICATIONS

"Optical Coherence Tomography: LightLab Imaging Starts US Cardiology Clinical Investigations," LightLab Imaging Technology, 2002.

(Continued)

*Primary Examiner* — Khadijeh A Vahdat
(74) *Attorney, Agent, or Firm* — Seager, Tufte & Wickhem, LLP

(57) ABSTRACT

A catheter and catheter system for treatment of a blood vessel of a patient include an elongate flexible catheter body with a radially expandable structure. A plurality of electrodes or other electrosurgical energy delivery surfaces can radially engage material to be treated when the structure expands. A material detector near the distal end of the catheter body may measure circumferential material distribution, and a power source selectively energizes the electrodes to eccentrically treat of a body lumen.

18 Claims, 39 Drawing Sheets

Related U.S. Application Data continuation of application No. 11/864,779, filed on Sep. 28, 2007, now Pat. No. 9,125,666, which is a division of application No. 10/938,138, filed on Sep. 10, 2004, now Pat. No. 7,291,146.

(60) Provisional application No. 60/502,515, filed on Sep. 12, 2003.

(51) Int. Cl.
A61B 18/00 (2006.01)
A61B 90/00 (2016.01)

(52) U.S. Cl.
CPC ............ *A61B 2018/0016* (2013.01); *A61B 2018/0022* (2013.01); *A61B 2018/0041* (2013.01); *A61B 2018/00214* (2013.01); *A61B 2018/00267* (2013.01); *A61B 2018/00577* (2013.01); *A61B 2018/00601* (2013.01); *A61B 2018/00654* (2013.01); *A61B 2018/1861* (2013.01); *A61B 2090/373* (2016.02); *A61B 2090/374* (2016.02); *A61B 2090/376* (2016.02); *A61B 2090/3784* (2016.02); *A61B 2218/002* (2013.01); *A61B 2218/007* (2013.01)

(58) Field of Classification Search
CPC .. A61B 2018/00214; A61B 2018/0022; A61B 2018/00267; A61B 2018/0041; A61B 2018/00577; A61B 2018/00601; A61B 2018/00654; A61B 2018/1861; A61B 2090/373; A61B 2090/374; A61B 2090/376; A61B 2090/3784; A61B 2218/002; A61B 2218/007
USPC ..................................................... 606/28–50
See application file for complete search history.

(56) References Cited

U.S. PATENT DOCUMENTS

| | | | |
|---|---|---|---|
| 5,454,370 A | 10/1995 | Avitall | |
| 5,487,385 A | 1/1996 | Avitall | |
| 5,755,760 A | 5/1998 | Maguire et al. | |
| 5,882,333 A | 3/1999 | Schaer et al. | |
| 5,891,134 A | 4/1999 | Goble et al. | |
| 6,023,638 A | 2/2000 | Swanson | |
| 6,056,746 A | 5/2000 | Goble et al. | |
| 6,711,444 B2 | 3/2004 | Koblish | |
| 8,920,414 B2 | 12/2014 | Stone et al. | |
| 2002/0013581 A1* | 1/2002 | Edwards | A61B 18/1477 606/41 |
| 2002/0139379 A1 | 10/2002 | Edwards et al. | |
| 2002/0165532 A1 | 11/2002 | Hill, III et al. | |
| 2003/0153905 A1* | 8/2003 | Edwards | A61B 18/1492 606/41 |
| 2004/0167509 A1 | 8/2004 | Taimisto | |
| 2004/0193239 A1 | 9/2004 | Falwell et al. | |
| 2007/0129720 A1* | 6/2007 | Demarais | A61B 18/18 606/41 |

FOREIGN PATENT DOCUMENTS

| | | |
|---|---|---|
| JP | 2004503265 A | 2/2004 |
| WO | 1995017151 A1 | 6/1995 |
| WO | 1999000060 A1 | 1/1999 |

OTHER PUBLICATIONS

"Carrington, "Future of CVI: It's All About the Plaque"", Diagnostic Imaging Special Edition Forum [online] [retrieved on Sep. 3, 2003] Retrieved from the Internet: <http://dimag.com/specialedition/cardiacimg.shtml> 5 pages total.

RuSanTan, et al. "Power versus temperature-controlled ablation of supraventricular tachycardia," Asian Cardiovasc. Thorac. Ann., vol. 9 (Jan. 1, 2001), XP055051048.

Schauerte et al., "Catheter Ablation of Cardiac Autonomic Nerves for Prevention of Vagal Atrial Fibrillation," Circulation, 2000, p. 2774-2780, vol. 102.

Scheller, "Coronary Paclitaxel Added to Contrast Media Inhibits In-Stent Restenosis of Porcine Coronary Arteries", Abstract #2227, AHA (2002), 1 page total.

Slager et al., "Vaporization of Atherosclerotic Plaques by Spark Erosion," J Am Coll Cardiol, 1985, p. 21-25.

Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.

Summons to Attend Oral Proceedings of EP Patent Application No. 07844424.7, dated Jul. 5, 2012, 7 pages total.

Supplementary Partial European Search Report of Application No. 04816863.7, dated May 8, 2009, 7 pages total.

European Search Report and Search Opinion of EP Patent Application No. 11191822.3, dated Jun. 13, 2012, 13 pages total.

Partial European Search Report of EP Patent Application No. 12154069.4, dated May 10, 2012, 5 pages total.

European Search Report and Search Opinion of EP Patent Application No. 07844417.1, dated Nov. 5, 2009.

European Search Report and Search Opinion of EP Patent Application No. 07844421.3, dated Jan. 4, 2010, 15 pages total.

European Search Report and Search Opinion of EP Patent Application No. 07844424.7, dated Nov. 11, 2009, 11 pages total.

European Search Report and Search Opinion of EP Patent Application No. 12151957.3, dated Apr. 16, 2012, 8 pages total.

European Search Report and Search Opinion of EP Patent Application No. 12154120.5, dated May 8, 2012, 8 pages total.

European Search Report and Search Opinion of EP Patent Application No. 12155447.1, dated May 10, 2012, 6 pages total.

Examiner's First Report of Australian Patent Application No. 2007310988, dated May 23, 2012, 4 pages total.

Examiners Report of Canadian Patent Application No. 2539026, dated Feb. 6, 2012, 4 pages total.

Extended European Search Report and Search Opinion of EP Patent Application No. 12154069.4, dated Sep. 17, 2012, 13 pages total.

Final Decision of Rejection issued in Japanese Patent Application No. 2006-526351, dated Jan. 18, 2011, 4 pages total.

Formal Inquiry issued in Japanese Patent Application No. 2006-526351, dated Jan. 17, 2012, 5 pages total. [Translation 5 pages].

International Search Report and Written Opinion of PCT Application No. PCT/US2009/064027, dated Jan. 19, 2010, 8 pages total.

International Search Report and Written Opinion of PCT Application No. PCT/US2009/064465, dated Jan. 13, 2010, 12 pages total.

International Search Report and Written Opinion of PCT/US2010/034789, dated Jul. 9, 2010, 13 pages total.

International Search Report and Written Opinion of PCT/US2011/000661, dated Nov. 18, 2011, 13 pages total.

International Search Report of PCT Application No. PCT/US2009/057728, dated Nov. 30, 2009, 09 pages total.

Notice of the Reason for Refusal issued in Japanese Patent Application No. 2006-526351, dated Apr. 27, 2010, 6 pages total.

Notice of the Reason for Refusal issued in Japanese Patent Application No. 2006-526351, dated Sep. 18, 2012, 20 pages total.

Notice of the Reason for Refusal issued in Japanese Patent Application No. 2009-533544, dated Jun. 19, 2012, 6 pages total.

Partial European Search Report of EP Patent Application No. 11191822.3, dated Mar. 19, 2012, 7 pages total.

Office Action issued in Australian Patent Application No. 2010248955, dated Sep. 13, 2012, 4 pages total.

Office Action issued in Chinese Patent Application No. 200480030163.9, dated Aug. 31, 2007, 8 pages total.

Office Action issued in Chinese Patent Application No. 200480030163.9, dated Jan. 16, 2009, 8 pages total.

Office Action issued in Chinese Patent Application No. 200480030163.9, dated Jul. 31, 2009, 5 pages total.

Office Action issued in Chinese Patent Application No. 200480030163.9, dated Mar. 28, 2008, 7 pages total.

(56) References Cited

OTHER PUBLICATIONS

Office Action issued in Chinese Patent Application No. 200680016424.0, dated Apr. 13, 2010, 10 pages total.
Office Action issued in Chinese Patent Application No. 201110031923.X, dated Sep. 6, 2012, 11 pages total.
Office Action issued in Chinese Patent Application No. 20111031923.X, dated May 22, 2012, 10 pages total.
Office Action issued in Chinese Patent Application No. 20111031923.X, dated Nov. 17, 2011, 16 pages total.
Office Action issued in European Application No. 04816863.7, dated Dec. 5, 2011, 4 pages total.
Office Action issued in European Application No. 04816863.7, dated Jan. 22, 2010, 6 pages total.
Office Action issued in European Application No. 04816863.7, dated Jun. 4, 2010, 5 pages total.
Office Action issued in European Application No. 07844421.3, dated Aug. 23, 2012, 5 pages total.

\* cited by examiner

SELECTABLE ECCENTRIC REMODELING AND/OR ABLATION

CROSS-REFERENCES TO RELATED APPLICATIONS

This application is a continuation of U.S. patent application Ser. No. 13/831,634, filed Mar. 15, 2013, now U.S. Pat. No. 10,188,457, which is a continuation of U.S. patent application Ser. No. 11/864,779, filed on Sep. 28, 2007, now granted as U.S. Pat. No. 9,125,666, which is a divisional of U.S. patent application Ser. No. 10/938,138, filed on Sep. 10, 2004, now U.S. Pat. No. 7,291,146, which claims the benefit under 35 USC 119(e) of U.S. Provisional Patent Application No. 60/502,515, filed on Sep. 12, 2003, the full disclosures of which are incorporated herein by reference.

BACKGROUND OF THE INVENTION

1. Field of the Invention

The present invention is generally related to medical devices, systems, and methods. In an exemplary embodiment, the invention provides catheter-based remodeling and/or removal of atherosclerosis plaque built-up in an artery to improve blood flow, often without balloon angioplasty, stenting, and/or dilation. The structures of the invention allow image-guided eccentric atherosclerotic material remodeling and/or removal typically using electrosurgical energy, optionally using electrosurgical ablation, often in a controlled environment zone within the blood vessel, and ideally with a co-located intravascular imaging capability. Related embodiments have applications in a variety of body lumens, including urinary, reproductive, gastrointestinal, and pulmonary obstructive material removal, optionally for removing or decreasing tumors, cysts, polyps, and the like.

Physicians use catheters to gain access to and repair interior tissues of the body, particularly within the lumens of the body such as blood vessels. For example, balloon angioplasty and other catheters often are used to open arteries that have been narrowed due to atherosclerotic disease.

Balloon angioplasty is often effective at opening an occluded blood vessel, but the trauma associated with balloon dilation can impose significant injury, so that the benefits of balloon dilation may be limited in time. Stents are commonly used to extend the beneficial opening of the blood vessel.

Stenting, in conjunction with balloon dilation, is often the preferred treatment for atherosclerosis. In stenting, a collapsed metal framework is mounted on a balloon catheter which is introduced into the body. The stent is manipulated into the site of occlusion and expanded in place by the dilation of the underlying balloon. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions.

Restenosis or a subsequent narrowing of the body lumen after stenting has occurred in a significant number of cases. More recently, drug coated stents (such as Johnson and Johnson's Cypher™ stent, the associated drug comprising Sirolimus™) have demonstrated a markedly reduced restenosis rate, and others are developing and commercializing alternative drug eluting stents. In addition, work has also been initiated with systemic drug delivery (intravenous or oral) which may also improve the procedural angioplasty success rates.

While drug eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

A variety of modified restenosis treatments or restenosis-inhibiting occlusion treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

A number of alternatives to stenting and balloon angioplasty so as to open stenosed arteries have also been proposed. For example, a wide variety of atherectomy devices and techniques have been disclosed and attempted. Despite the disadvantages and limitations of angioplasty and stenting, atherectomy has not gained the widespread use and success rates of dilation-based approaches. Still further disadvantages of dilation have come to light. These include the existence of vulnerable plaque, which can rupture and release materials that may cause myocardial infarction or heart attack.

In light of the above, it would be advantageous to provide new devices, systems, and methods for remodeling and/or removal of atherosclerotic material and other occlusions of the lumens of the body, and particularly from blood vessels. It would further be desirable to enable the removal of these occlusive materials without having to resort to the trauma of a dilation, and to allow the opening of blood vessels and other body lumens which are not suitable for stenting.

BRIEF SUMMARY OF THE INVENTION

In a first aspect, the invention provides a catheter system for eccentric remodeling of atherosclerotic material of a blood vessel of a patient. The system comprises an elongate flexible catheter body having a proximal end and a distal end with an axis therebetween. A radially expandable structure is disposed near the end of the catheter body, and a plurality of energy delivery surfaces are each oriented radially when the expandable structure expands. An atherosclerotic material detector is disposed for circumferential atherosclerotic material detection. A power source is electrically coupled to the energy delivery surfaces. The power source energizes the energy delivery surfaces so as to eccentrically remodel the detected atherosclerotic material.

The power source will often selectively energize a subset of the energy delivery surfaces so as to effect eccentric remodeling. The catheter body may have a lumen extending between the proximal and distal ends, and an aspiration connector may be in fluid communication with the lumen at the proximal end of the catheter body. Proximal and distal debris barriers may be disposed proximally and distally of the energy delivery surfaces, respectively, and an aspiration port may be disposed between the proximal and distal barriers for removal of debris during atherosclerotic material remodeling.

The atherosclerotic material detector may include an intravascular ultrasound catheter disposed in the lumen of the catheter body, an intravascular optical coherence tomography catheter disposed in the lumen, an intravascular catheter having an MRI antenna disposed in the lumen, or the like. Alternative detectors may employ any of a variety of non-invasive imaging modalities, including external systems making use of X-rays, CT systems, non-invasive MRI or NMR systems, or the like, so that the detector may not be disposed in the blood vessel. In some embodiments, a brachytherapy catheter or other restenosis inhibitor may be advanced distally within the lumen.

The radially expandable body may comprise a plurality of flexible struts, and the energy delivery surfaces may define a circumferentially oriented array, with the energy delivery surfaces often comprising electrodes or microwave antennas. Struts of the radially expandable structure may have perforations disposed therebetween so as to define an expandable basket. The basket may have proximal and distal portions with intermediate portion disposed therebetween. The array of electrodes may be supported along the intermediate portion so as to engage adjacent atherosclerotic material when the basket is expanded within the blood vessel. The electrodes may comprise conductive surfaces of an electrode structure mounted to a separately formed basket strut. In other embodiments, electrode surfaces may be formed as part of the expandable structure. For example, the electrodes may comprise a localized widening of an associated strut, often disposed near center of a length of the strut. The expandable structure may comprise Nitinol™, and the remaining surface of the Nitinol strut may be insulated. For example, the surface may be coated with a high temperature polymer (such as a polyimide or the like). Other coatings may alternatively be used, including polyurethane. The struts may be electrically insulated from each other, so that each strut can be used to conduct energy to an electrode surface associated with the strut from a conductor extending proximally from the strut so as to independently couple each electrode surface to a controller.

A distal membrane may be deployable within the blood vessel distally of the electrode so as to inhibit distal movement of debris. A proximal membrane may be deployable proximally of the electrode so as to inhibit proximal movement of the debris. The membranes may inhibit blood interaction with the remodeling process, for example, during ablation of the atherosclerotic material. In other embodiments, power supplied to the energy delivery surfaces may be limited so as to inhibit debris generation, for example, by denaturing the atherosclerotic material, by melting of atherosclerotic material inside layers of the artery, by shrinking of atherosclerotic material inside layers of the artery (during treatment and/or in a tissue healing response), and the like. In some embodiments, the distal membrane may be supported by the distal portion of the basket so as to expand radially therewith. The proximal membrane may be supported by the proximal portion of the basket so as to expand radially therewith. At least one of the proximal and distal membranes may comprise a lumen axially off-set from the basket.

While some embodiments may have a single monopolar electrode or two or more monopolar or bipolar electrodes, the electrodes may comprise an array of at least three alternatively selectable electrodes distributed circumferentially about the axis, often comprising six or more electrodes. A controller may couple the power source to the electrode array so as to selectively energize that eccentric subset of the electrode array in response to the detected atherosclerotic material. A controller may selectively energize a subset of the energy directing surfaces by directing RF energy and/or microwave energy thereto. The atherosclerotic material detector may comprise an ultrasound transducer or optical coherence reflectometer. Along with stand-alone structures that are insertable into a lumen of the catheter, these detectors may also be integrated into the catheter structure. A display may be coupled to the atherosclerotic material detector to show an image of circumferential atherosclerotic material thickness distributed about the catheter axis.

In another aspect, the invention provides a catheter system for eccentric remodeling and/or removal of atherosclerotic material from a blood vessel of a patient. The system comprises an elongate flexible catheter body having a proximal end and a distal end with an axis therebetween. A radially expandable structure is disposed near the distal end of the catheter body. A plurality of electrodes are oriented to be radially urged against atherosclerotic material when the expandable structure expands. An atherosclerotic material detector or imaging sensor is disposed near the distal end of the catheter body for circumferential identification and measurement of atherosclerotic material. A power source is electrically coupled to the electrodes. The power source energizes the electrodes so as to eccentrically remove and/or ablate the measured atherosclerotic material.

The catheter body will often have a lumen extending between the proximal end and the distal end. The lumen may be used as an aspiration lumen, for example, using an aspiration source in fluid communication with the lumen at the proximal end of the catheter body. Proximal and distal ablation debris barriers may be disposed proximally and distally of the electrodes, respectively, with an aspiration port disposed between the proximal and distal barriers for removal of ablation debris during atherosclerotic material ablation. The atherosclerotic material detector may comprise an ultrasound transducer of an intravascular ultrasound catheter, with the intravascular ultrasound catheter disposed in the lumen. Alternatively, other imaging modalities may be employed, including intravascular optical coherence tomography. Imaging or atherosclerotic material detecting capabilities might also be incorporated into the catheter body in some embodiments, with circumferential atherosclerotic thicknesses often being measured. An irrigation lumen may extend between the proximal end of the catheter body and the distal end of the catheter body, facilitating an enhanced local ablation environment adjacent the electrodes. A restenosis inhibitor may be advanced within the lumen, the restenosis inhibitor optionally comprising an intravascular radiation catheter, restenosis inhibiting drugs, or the like.

The radially expandable body may comprise a plurality of flexible members or struts, the electrodes optionally defining a circumferential electrode array. The struts may have perforations or openings therebetween so as to define an expandable basket. The array of electrodes may be supported along an intermediate portion of the basket and oriented radially so as to engage adjacent atherosclerotic material when the basket is expanded within a blood vessel. An aspiration port in fluid communication with an interior of the basket may facilitate removal of any ablation debris and tissue vaporization gasses, and may inhibit release of these byproducts of ablation within the blood vessel, and fluid flowing within the basket may act as a cooling fluid to limit collateral tissue damage. A distal membrane or barrier deployable within the blood vessel distally of the electrodes may inhibit distal movement of any ablation debris, while a proximal membrane or membrane deployable proximally of the electrodes may inhibit proximal movement of any ablation debris. Such member(s) may also reduce or inhibit blood flow within a localized remodeling and/or ablation environment. The distal membrane may be supported by the distal portion of the basket so as to expand radially therewith, and/or the proximal membrane may be supported by the proximal portion of the basket so as to expand radially therewith. Suitable membranes include, for example, one or more balloons axially offset from the basket within the blood vessel, or a braided superelastic material such as Nitinol™ dipped in silicone, polyurethane, PTFE, or another elastic material. In some embodiments, the membrane may be at least in part integrated with the basket.

The electrodes will often comprise an array of at least three, often comprising at least six alternatively selectable electrodes distributed circumferentially about the axis of the catheter body. The arrays of electrodes may be axisymmetric, with an eccentric treatment orientation being selected without physically rotating the array by selectively pairing electrodes of the array. A controller couples the power source to the electrode array for selectively energizing an eccentric subset of the electrode array in response to the measured atherosclerotic material. Exemplary electrodes may comprise stainless steel soldered to copper wires, with the copper wires insulated from supporting elements of associated expandable basket elements. Alternative electrodes may comprise platinum (which also allows the electrode to serve as a radiopaque marker). The electrode/basket assembly may be, for example, coated with a high temperature polymer, such as a polyimide. An exemplary electrode array includes alternating axially offset electrodes, and the controller will often direct RF bipolar power between pairs of the energized subset of electrodes, the pairs optionally comprising circumferentially offset electrodes, adjacent axially aligned electrodes, or alternating between axially and circumferentially offset electrodes. In some embodiments monopolar energy may be directed to selected electrodes, with the circuit being completed by a patient ground. More generally, each electrode will typically comprise a metallic body affixed to an adjacent strut of the expandable structure by a polymer with an associated conductor extending proximally from the electrode so as to electrically couple the electrode surface to the controller.

The exemplary atherosclerotic material detector will comprise an ultrasound transducer of an intravascular ultrasound catheter, a sensor of an intravascular optical coherence tomography catheter, or the like. A display may be provided to show an image of circumferential sclerotic material thickness about the catheter axis, the display and/or imaging catheter signals optionally comprising indicia of orientation for rotationally registering the selected electrodes to the measurements. Suitable indicia may comprise a "key" or distinguishable image of at least one expandable member or marker.

In another aspect, the invention provides a catheter for atherosclerotic material removal from the blood vessel of a patient. The catheter comprises an elongate flexible catheter body having a proximal end and a distal end with an axial aspiration lumen therebetween. A radially expandable basket near the distal end of the catheter body has a proximal portion and a distal portion with an intermediate portion disposed therebetween. A circumferential electrode array is distributed about the intermediate portion of the radially expandable basket so as to ablate adjacent atherosclerotic material when the basket expands within the blood vessel. An aspiration port provides fluid communication between the aspiration lumen and an interior of the basket. A distal membrane supported by the distal portion of the basket inhibits distal movement of ablation debris when the basket is expanded within the blood vessel. A proximal membrane supported by the proximal portion of the basket inhibits proximal movement of ablation debris when the basket is expanded within the blood vessel.

In a first method aspect, the invention provides a method for remodeling eccentric atherosclerotic material of a blood vessel of a patient. The method comprises positioning a working end of a catheter within the blood vessel adjacent the atherosclerotic material, the catheter defining an axis. The catheter is radially expanded so as to engage at least one energy delivery surface of the catheter against the atherosclerotic material. A circumferential distribution of the atherosclerotic material about the axis of the catheter is determined. Electrosurgical energy is directed from the at least one energy delivery surface eccentrically relative to the axis of the catheter in response to the determined atherosclerotic material distribution.

Remodeling of the atherosclerotic material may comprise ablation, removal, shrinkage, melting, denaturing, and/or the like of the atherosclerotic material. For example, relatively low power RF energy may be used to heat the atherosclerotic material until it melts, the material optionally being redistributed along the artery wall, inside layers of the vessel, or the like. Optionally, the atherosclerotic material may comprise a vulnerable plaque. Vulnerable plaques (and/or blood vessels in which vulnerable plaque is a concern) may be treated using RF energy to mildly heat the cap and underlying lipid-rich pool of the vulnerable plaque to a temperature in a range from about 50 to about 60° Celsius. This may be performed so as to generate thickening of the cap, often as an immune response to heating. Such thickening may potentially result in restenosis, and cap thickening and/or restenosis may be limited by accurate control of the RF energy, the use of anti-restenotic drugs (such as Rapamycin™ or the like). In addition to vulnerable plaque stabilization, the invention may be employed to eliminate vulnerable plaques, optionally by heating of the lipid-rich pool to a temperature of at least around 90° Celsius. Preferably, heating of the blood vessel will be performed so as to limit a temperature of an adventitia or outer layer of the blood vessel to below about 63° Celsius so as to inhibit collagen shrinkage and vessel collapse. In contrast, mild RF energy may be applied to the atherosclerotic material so as to denature the material and result in shrinkage of the material during or after treatment. Shrinkage of atherosclerotic material may lead to larger open vessel lumens and improved blood flow.

When remodeling of atherosclerotic plaques comprises ablation of atherosclerotic materials, any thrombolitic debris generated may be restrained and/or evacuated. Where ablation generates non-thrombolitic debris, or where remodeling is performed so as to inhibit debris generation, debris restraining and evacuation may be unnecessary.

Electrosurgical energy directed by the one or more energy delivery surfaces will often comprise RF and/or microwave electrical energy. The circumferential distribution of atherosclerotic material may be determined using intravascular or non-invasive techniques. The electrosurgical energy may be directed eccentrically without rotating the energy delivery surfaces about the catheter axis by energizing a subset of the electrodes. The subset of electrodes may be selected in response to the determined atherosclerotic material distribution. Selected electrodes may be rotationally registered with the atherosclerotic material distribution, for example, with reference to one or more structures of the expandable basket having a distinguishable image. For example, a strut of the electrode arbitrarily identified as electrode 1 may have one radiopaque marker or other distinguishable image, and a strut of an electrode referenced as electrode 2 may have two radiopaque markers or two distinguishable image features. This can help identify all of the electrodes, since electrode 1 is identifiable and the direction from electrode 1 to electrode 2 indicates a circumferential electrode count direction. A variety of alternative distinguishable features with integrated or separate circumferential electrode count orientation indicators may also be utilized. In some embodiments, registration may be performed automatically with reference to an electronic signal.

In yet another aspect, the invention provides a method for eccentric atherosclerotic material removal from a blood vessel of a patient. The method comprises positioning a working end of the catheter within the blood vessel and adjacent the atherosclerotic material. The catheter defines the axis. The catheter is radially expanded so as to engage a plurality of electrodes of the catheter against the atherosclerotic material. A circumferential distribution of the atherosclerotic material is measured about the axis of the catheter. RF energy is directed from the electrodes eccentrically relative to the axis of the catheter in response to the measured atherosclerotic material distribution.

DETAILED DESCRIPTION OF THE INVENTION

Figure 1A:
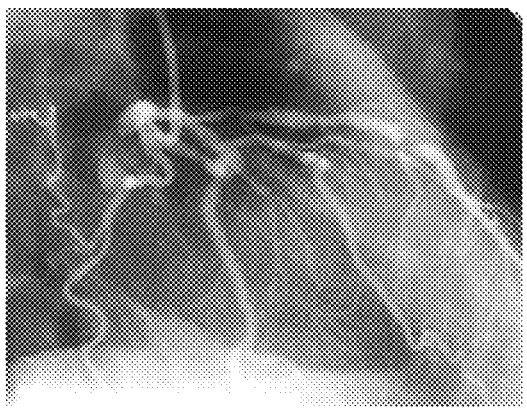
FIG. 1A illustrates diffuse atherosclerotic disease in which a substantial length of multiple blood vessels has limited effective diameters.

The present invention provides devices, systems, and methods to remodel a partially occluded artery in order to open the artery lumen and increase blood flow. Remodeling may involve the application of electrosurgical energy, typically in the form of RF and/or microwave electrical potentials to energy delivery surfaces such as electrodes, antennas, and the like. This energy will often be controlled so as to limit a temperature of target and/or collateral tissues, for example, limiting the heating of a fibrous cap of a vulnerable plaque or the intimal layer of an artery structure to a maximum structure in a range from about 50 to about 60° Celsius, by limiting the maximum temperature of an outer layer or adventitia of the blood vessel to no more than about 63° Celsius, limiting heating of a lipid-rich pool of a vulnerable plaque sufficiently to induce melting of the lipid pool while inhibiting heating of other tissues (such as an intimal layer or fibrous cap) to less than a temperature in a range from about 50 to about 60° Celsius so as to inhibit an immune response that might otherwise lead to restenosis, or the like. Relatively mild heating energies may be sufficient to denature and shrink atherosclerotic material during treatment, immediately after treatment, and/or more than one hour, more than one day, more than one week, or even more than one month after the treatment through a healing response of the tissue to the treatment so as to provide a bigger vessel lumen and improved blood flow.

In some embodiments, remodeling of the atherosclerotic plaque may comprise the use of higher energies to ablate and remove occlusive material from within body lumens, and particularly to remove atherosclerotic material from a blood vessel in order to improve blood flow. Ablation debris may be generated by such ablation, and the ablation debris may be thrombolitic or non-thrombolitic. Where thrombolitic debris is generated by ablation, that debris may be restrained, captured, and/or evacuated from the treatment site. Non-thrombolitic debris produced by ablation may not have to be restrained and/or evacuated from the vessel. The techniques of the invention will often provide electrosurgical capabilities, sensing or imaging suitable for measuring atheroma and/or vascular walls, and/or an emboli inhibitor. As atherosclerosis may be eccentric relative to an axis of the blood vessel over 50% of the time, possibly in as much as (or even more than) 75% of cases, the devices and methods of the present invention will often be particularly well suited for directing treatment eccentrically, often in response to circumferential atherosclerotic material detecting or imaging. While the methods and devices described herein allow such eccentric treatments, the devices can also be used for treatment of radially symmetric atherosclerosis by selectively directing energy in a radially symmetric pattern about an axis of the catheter or the like.

Hence, remodeling of atherosclerotic materials may comprise ablation, removal, shrinkage, melting, and the like of atherosclerotic and other plaques. Optionally, atherosclerotic material within the layers of an artery may be denatured so as to improve blood flow, so that debris will not necessarily be generated. Similarly, atherosclerotic materials within the arterial layers may be melted and/or treatment may involve a shrinking of atherosclerotic materials within the artery layers, again without necessarily generating treatment debris. The invention may also provide particular advantages for treatment of vulnerable plaques or blood vessels in which vulnerable plaque is a concern. Such vulnerable plaques may comprise eccentric lesions, and the present invention may be particularly well suited for identifying an orientation (as well as axial location) of the vulnerable plaque structure. The invention will also find applications for targeting the cap structure for mild heating (to induce thickening of the cap and make the plaque less vulnerable to rupture) and/or heating of the lipid-rich pool of the vulnerable plaque (so as to remodel, denature, melt, shrink, and/or redistribute the lipid-rich pool.

While the present invention may be used in combination with stenting and/or balloon dilation, the present invention is particularly well suited for increasing the open diameter of blood vessels in which stenting and balloon angioplasty are not a viable option. Potential applications include treatment of diffuse disease, in which atherosclerosis is spread along a significant length of an artery rather than being localized in one area. The invention may also provide advantages in treatment of vulnerable plaque or blood vessels in which vulnerable plaque is a concern, both by potentially identifying and avoiding treatment of the vulnerable plaque with selected eccentric and/or axial treatments separated from the vulnerable plaque, and by intentionally ablating and aspirating the cap and lipid-rich pool of the vulnerable plaque within a controlled environmental zone or region within the blood vessel lumen. The invention may also find advantageous use for treatment of tortuous, sharply-curved vessels, as no stent need be advanced into or expanded within the sharp bends of many blood vessel. Still further advantageous applications include treatment along bifurcations (where side branch blockage may be an issue) and in the peripheral extremities such as the legs, feet, and arms (where crushing and/or stent fracture failure may be problematic).

Figure 1B:
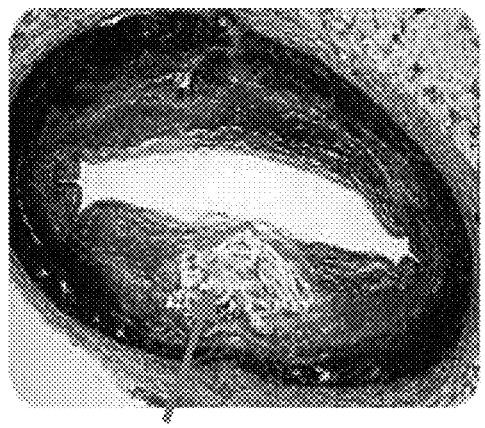
FIG. 1B illustrates vulnerable plaque within a blood vessel.
Figure 1C:
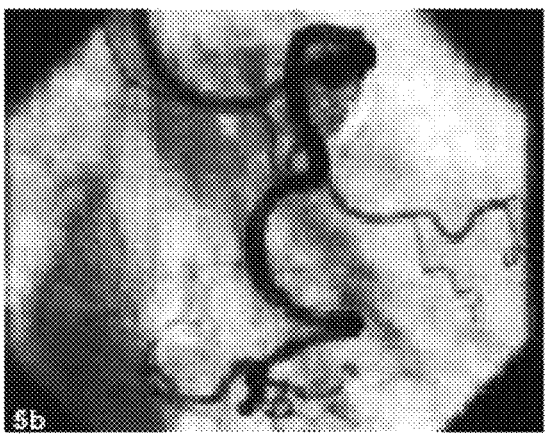
FIG. 1C illustrates the sharp bends or tortuosity of some blood vessels.
Figure 1D:
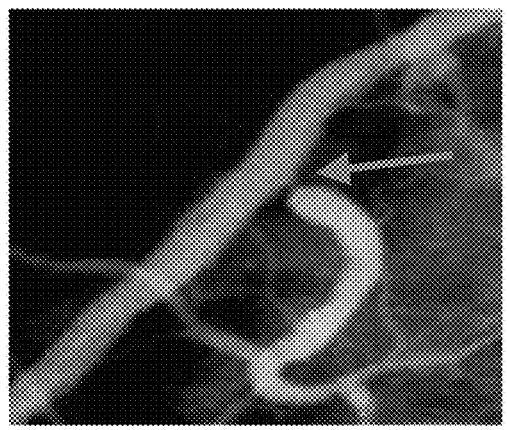
FIG. 1D illustrates atherosclerotic disease at a bifurcation.
Figure 1E:
FIG. 1E illustrates a lesion associated with atherosclerotic disease of the extremities.

Diffuse disease and vulnerable plaque are illustrated in FIGS. 1A and 1B, respectively. FIG. 1C illustrates vascular tortuosity. FIG. 1D illustrates atherosclerotic material at a bifurcation, while FIG. 1E illustrates a lesion which can result from atherosclerotic disease of the extremities.

Figure 1F:
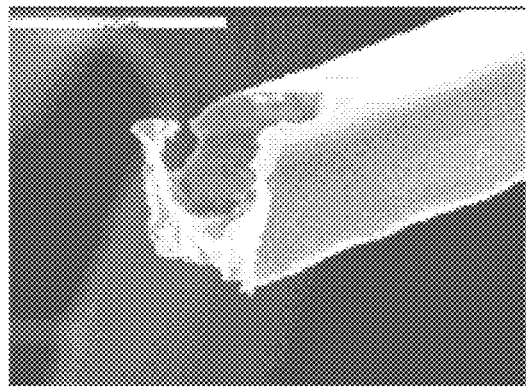
FIG. 1F is an illustration of a stent fracture or corrosion.

FIG. 1F illustrates a stent structural member fracture which may result from corrosion and/or fatigue. Stents may, for example, be designed for a ten-year implant life. As the population of stent recipients lives longer, it becomes increasingly likely that at least some of these stents will remain implanted for times longer than their designed life. As with any metal in a corrosive body environment, material degradation may occur. As the metal weakens from corrosion, the stent may fracture. As metal stents corrode, they may also generate foreign body reaction and byproducts which may irritate adjoining body tissue. Such scar tissue may, for example, result in eventual reclosure or restenosis of the artery.

Figure 1G:
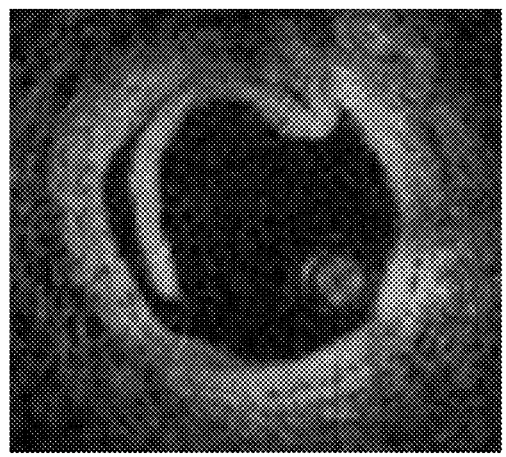
FIG. 1G illustrates a dissection within a blood vessel.
Figure 1H:
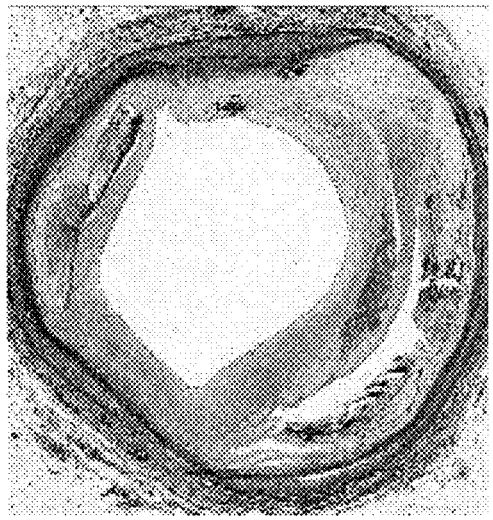
FIG. 1H illustrates a circumferential measurement of an artery wall around a healthy artery.
Figure 1I:
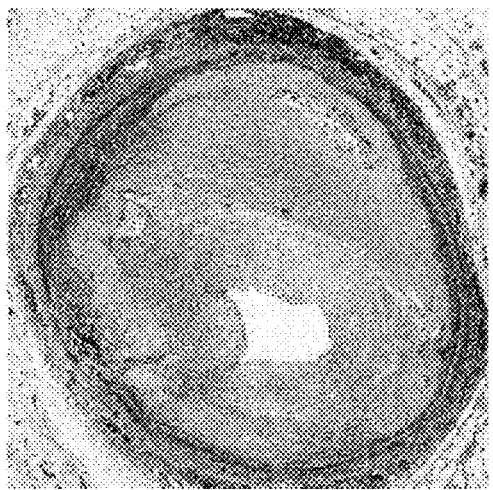
FIG. 1I illustrates circumferential distribution of atheroma about a restenosed artery.

Arterial dissection and restenosis may be understood with reference to FIGS. 1G through 1I. The artery comprises three layers, an endothelial layer, a medial layer, and an adventitial layer. During angioplasty, the inside layer may delaminate or detach partially from the wall so as to form a dissection as illustrated in FIG. 1G. Such dissections divert and may obstruct blood flow. As can be understood by comparing FIGS. 1H and 1I, angioplasty is a relatively aggressive procedure which may injure the tissue of the blood vessel. In response to this injury, in response to the presence of a stent, and/or in the continuing progression of the original atherosclerotic disease, the opened artery may restenose or subsequently decrease in diameter as illustrated in FIG. 1I. While drug eluting stents have been shown to reduce restenosis, the efficacy of these new structures several years after implantation has not be fully studied, and such drug eluting stents are not applicable in many blood vessels.

In general, the present invention provides a catheter which is relatively quick and easy to use by the physician. The catheter system of the present invention may allow arteries to be opened to at least 85% of their nominal or native artery diameter. In some embodiments, arteries may be opened to about 85%, and/or acute openings may be less than 85%. Rapid occlusive material removal may be effected using sufficient power to heat tissues locally to over about 100° C. so as to vaporize tissues, or more gentle remodeling may be employed.

The desired opening diameters may be achieved immediately after treatment by the catheter system in some embodiments. Alternatively, a milder ablation may be implemented, for example, providing to no more than a 50% native diameter when treatment is complete, but may still provide as much as 80 or even 85% or more native vessel open diameters after a subsequent healing process is complete, due to resorption of injured luminal tissues in a manner analogous to left ventricular ablation for arrhythmia and transurethral prostate (TURP) treatments. Such embodiments may heat at least some occlusive tissue to a temperature in a range from about 55° C. to about 80° C. In some embodiments, occlusive tissues may be heated to a maximum temperature in a range between about 93 and 95° C. In other embodiments described herein, heating may be controlled so as to provide tissue temperatures in a range between about 50 and 60° C., with some embodiments benefiting from maximum tissue temperatures of about 63° C. Still further treatments may benefit from treatment temperatures of about 90° C. Advantageously, the catheter systems and methods of the invention may be used without balloon angioplasty, thereby avoiding dissections and potentially limiting restenosis.

Figure 2:
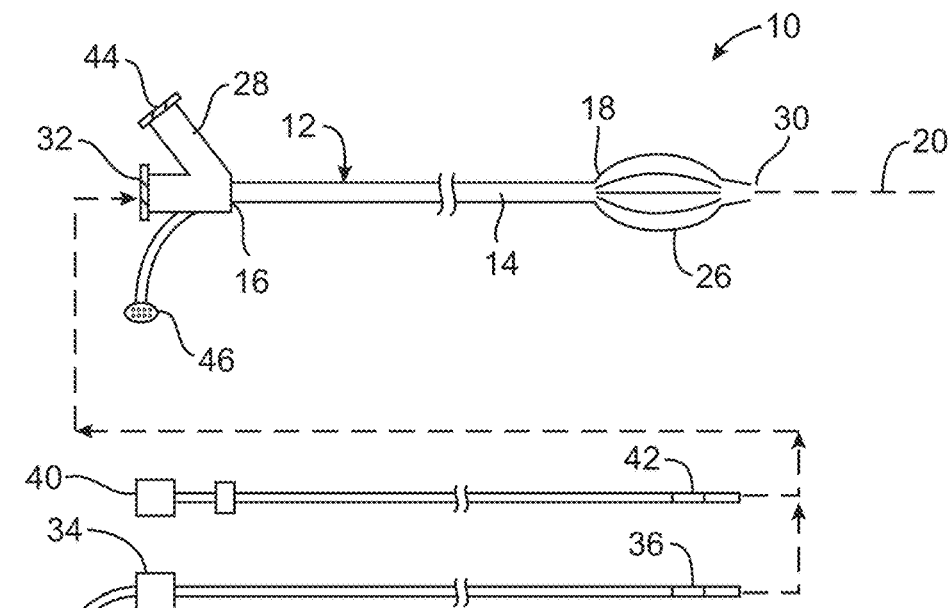
FIG. 2 schematically illustrates an atherosclerotic material catheter system according to the present invention.
Figure 2A:
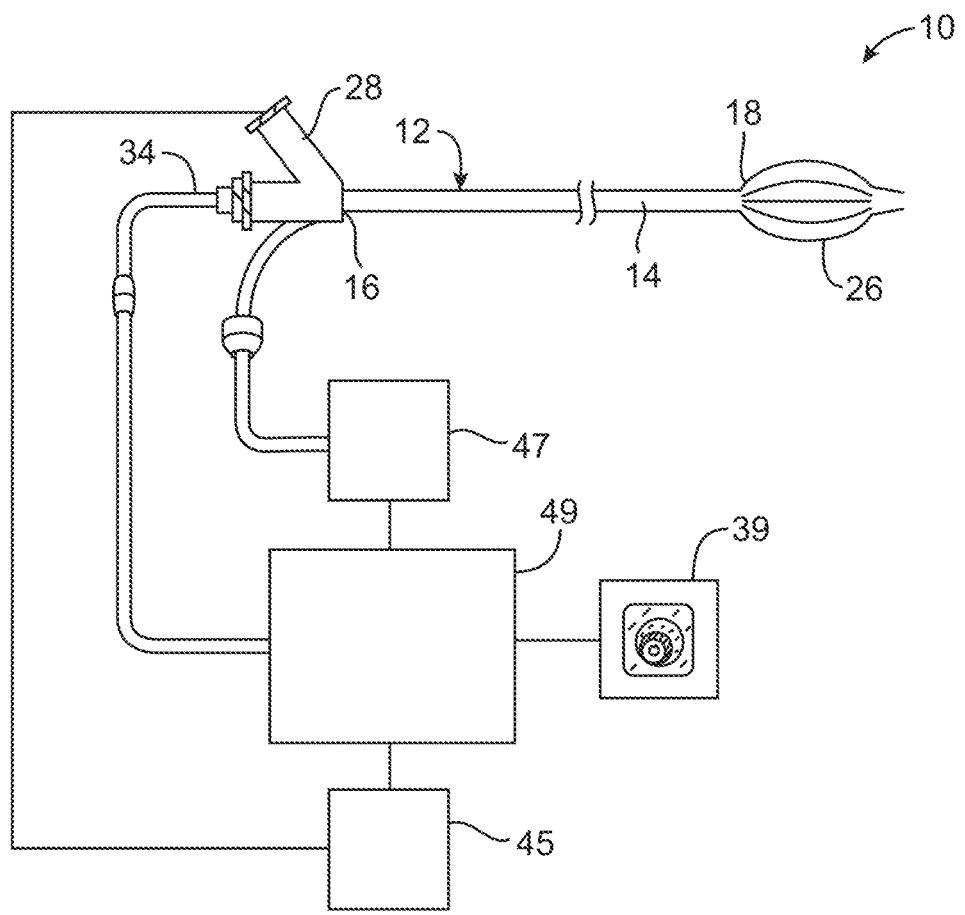
FIG. 2A schematically illustrates a catheter system for remodeling atherosclerotic material, the system including the catheter of FIG. 2.

An exemplary catheter system 10 is schematically illustrated in FIGS. 2 and 2A. A remodeling and/or ablation catheter 12 includes a catheter body 14 having a proximal end 16 and a distal end 18. Catheter body 14 is flexible and defines a catheter axis 20, and includes an aspiration lumen 22 and an irrigation lumen 24 (see FIG. 3). Still further lumens may be provided for a guidewire, imaging system, or the like as described below. Lumen 22 may be used for sensing and/or imaging of atheroma as well as aspiration.

Catheter 12 includes a radially expandable structure 26 adjacent distal end 18 and a housing 28 adjacent proximal end 16. A distal tip 30 may include an integral tip valve to seal aspiration lumen 22 and allow passage of guidewires, imaging and/or restenosis inhibiting catheters, and the like.

Proximal housing 28 includes a first connector 32 in fluid communication with aspiration lumen 22. Aspiration lumen 22 may have an aspiration port within expandable structure 26 so as to allow aspiration or aspiration of debris and gasses from within the expandable structure. Aspiration lumen 22 may also be used as an access lumen for guidewires, intravascular imaging catheters, and/or distally advancing intravascular radiation treatment catheters or restenosis inhibiting drugs. Hence, connector 32 may selectively accommodate an imaging catheter 34 having an atherosclerotic material detector 36 advanceable within catheter body 14 adjacent to and/or beyond distal end 18, the detector often comprising an intravascular ultrasound transducer, an optical coherent tomography sensor, an MRI antenna, or the like. An imaging connector 38 of imaging catheter 34 transmits imaging signals allowing circumferential measurement of atherosclerotic thicknesses about axis 20 to a display 39.

Connector 32 also accommodates a restenosis inhibiting treatment catheter 40, the treatment catheter here comprising an intravascular radiation catheter. Such a radiation catheter may include a radiation source 42 which can again be advanced distally within catheter body 14 to or beyond expandable structure 26.

Figure 3:
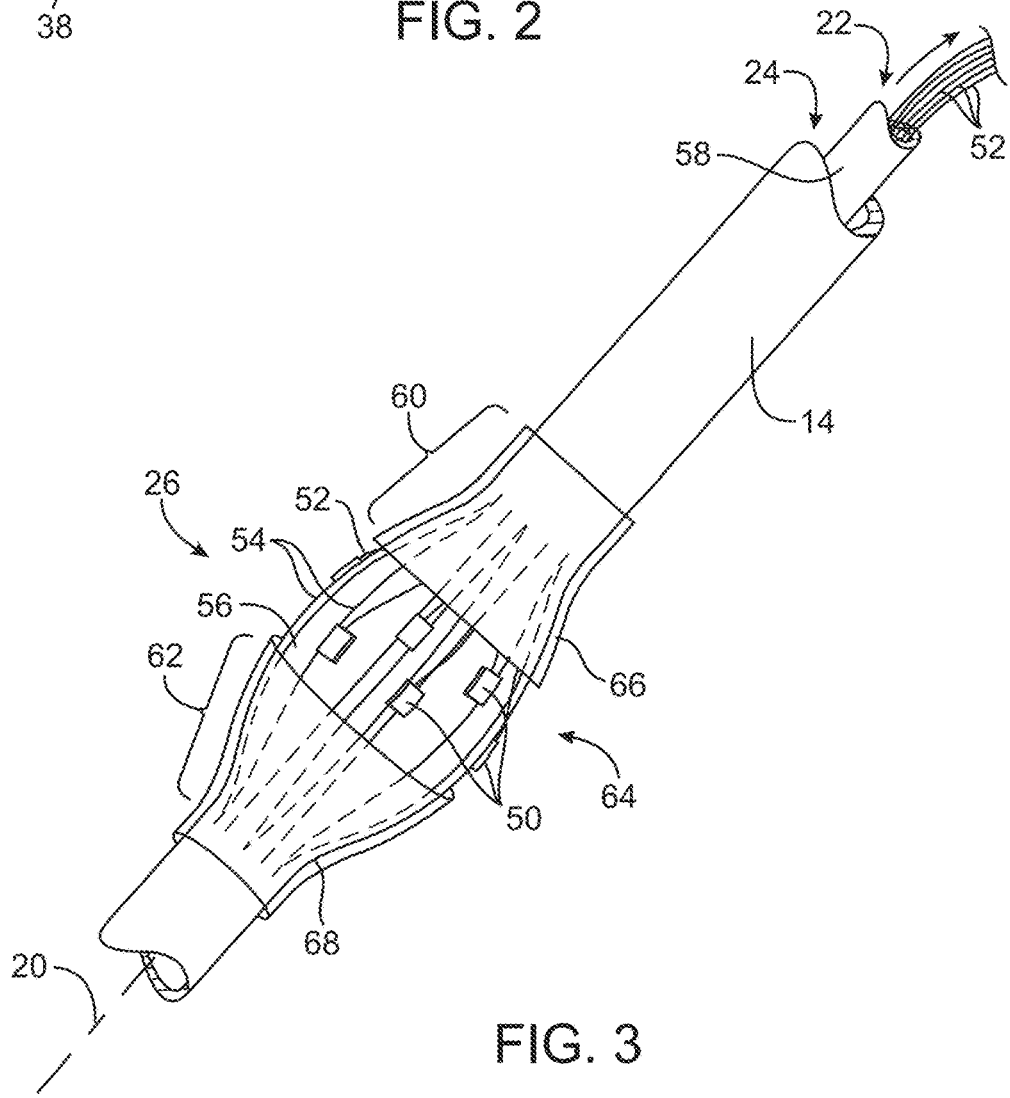
FIG. 3 illustrates an expandable basket and an associated electrode array of the catheter system of FIG. 2.

A second connector 44 of proximal housing 28 is in fluid communication with irrigation lumen 24 (see FIG. 3). Second connector 44 may be coupled to an irrigation fluid source for introducing conductive or non-conductive liquids, gases, or the like, ideally for introducing gas or heparinized saline. Both first and second connectors 32, 44 may optionally comprise a standard connector such as a Luer-Loc™ connector. In FIG. 2A connector 44 is schematically shown coupled to an aspiration vacuum source/infusion fluid source 45.

Referring now to FIGS. 2, 2A, and 3, proximal housing 28 also accommodates an electrical connector 46. Connector 46 includes a plurality of electrical connections, each electrically coupled to an electrode 50 via a dedicated conductor 52. This allows a subset of electrodes 50 to be easily energized, the electrodes often being energized with bipolar or monopolar RF energy. Hence, electrical connector 46 will often be coupled to an RF generator via a controller 47, with the controller allowing energy to be selectively directed to an eccentric portion of an engaged luminal wall. When monopolar RF energy is employed, patient ground may (for example) be provided by an external electrode or an electrode on catheter body 14. A processor 49 may manipulate signals from imaging catheter 34 to generate an image on display 39, may coordinate aspiration, irrigation, and/or treatment, and may automatically register the treatment with the image.

Expandable structure 26 is illustrated in more detail in FIG. 3. Expandable structure 26 may expand resiliently when released from within a restraining sheath, or may expand by pulling tip 30 toward distal end 18 (see FIG. 2), optionally using a pullwire, an inner catheter body 58, or the like. Expandable structure 26 here comprises a perforate structure or basket having a series of structural struts or elements 54 with opening or perforations 56 therebetween. Perforations 56 may be formed, for example, by cutting elongate slits in a flexible tube material, or the basket may be formed by braiding elongate wires or ribbons or the like.

Expandable structure 26 generally includes a proximal portion 60, a distal portion 62, and an intermediate portion 64 therebetween. Each electrode 50 is mounted on an associated basket element 54 along intermediate portion 64, with an associated conductor 52 extending proximally from the electrode. Electrodes 50 are distributed circumferentially about axis 20 in an array, adjacent electrodes preferably being axially offset, ideally being staggered or alternating between proximal and distal axial locations. This allows bipolar energy to be directed between adjacent circumferential (axially offset) electrodes between adjacent distal electrodes, between adjacent proximal electrodes, and the like.

Figure 12:
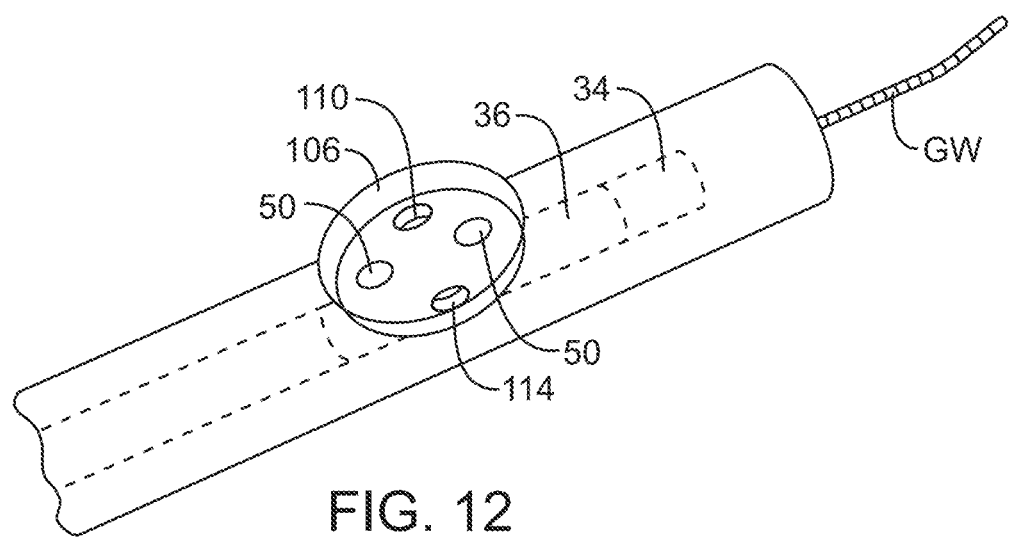
FIGS. 11-21 schematically illustrate alternative catheters and catheter systems for use in the methods described herein.
Figure 11:
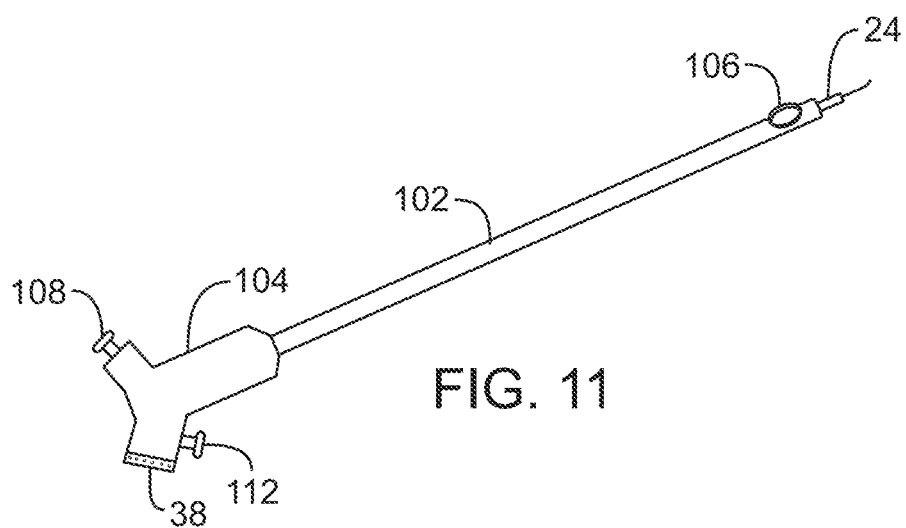
Figure 13:
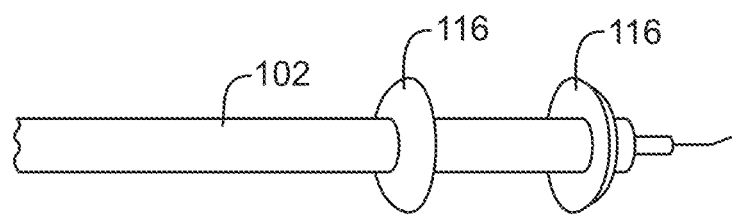

In the exemplary embodiment, proximal and distal barriers 66, 68 expand radially with proximal and distal portions 60, 62 of expandable structure 26. Barriers 66, 68 inhibit any ablation debris and gases generated adjacent electrodes 50 from traveling within the body lumen beyond catheter 12. Barriers 66, 68 also allow an at least partially isolated ablation environment to be established within the body lumen, for example, by replacing blood within a blood vessel with a more advantageous fluid environment for limiting charring of the electrodes and the like. Alternative barriers may be provided instead of (or in combination with) barriers 66, 68, including one or more balloons axially offset from expandable member 26, elastic lips as shown in FIG. 11-13, or the like. In other embodiments remodeling may be effected without generating significant thermolytic ablation debris and/or a desired treatment environment may be provided with localized irrigation and/or aspiration flows so that some systems may forego the use of barriers.

Figure 4:
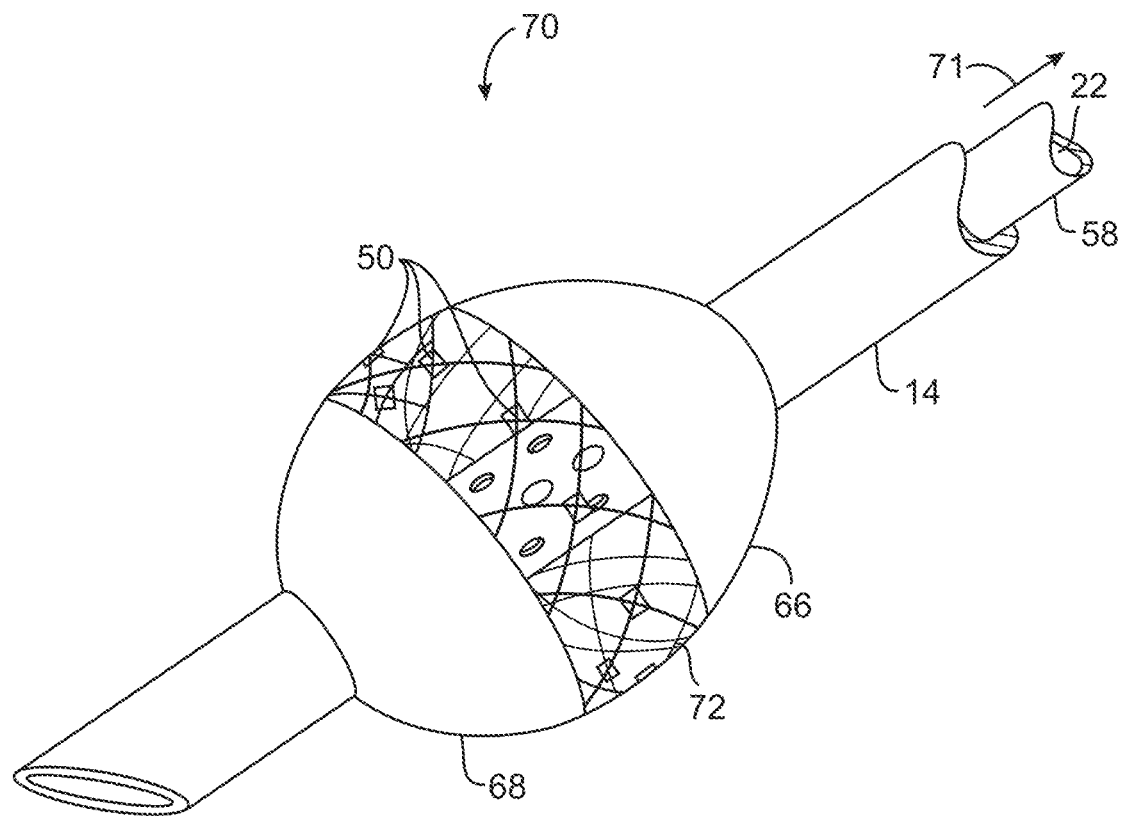
FIGS. 4 and 5 illustrate alternative basket structures for use with the catheter system of FIG. 2.
Figure 5:
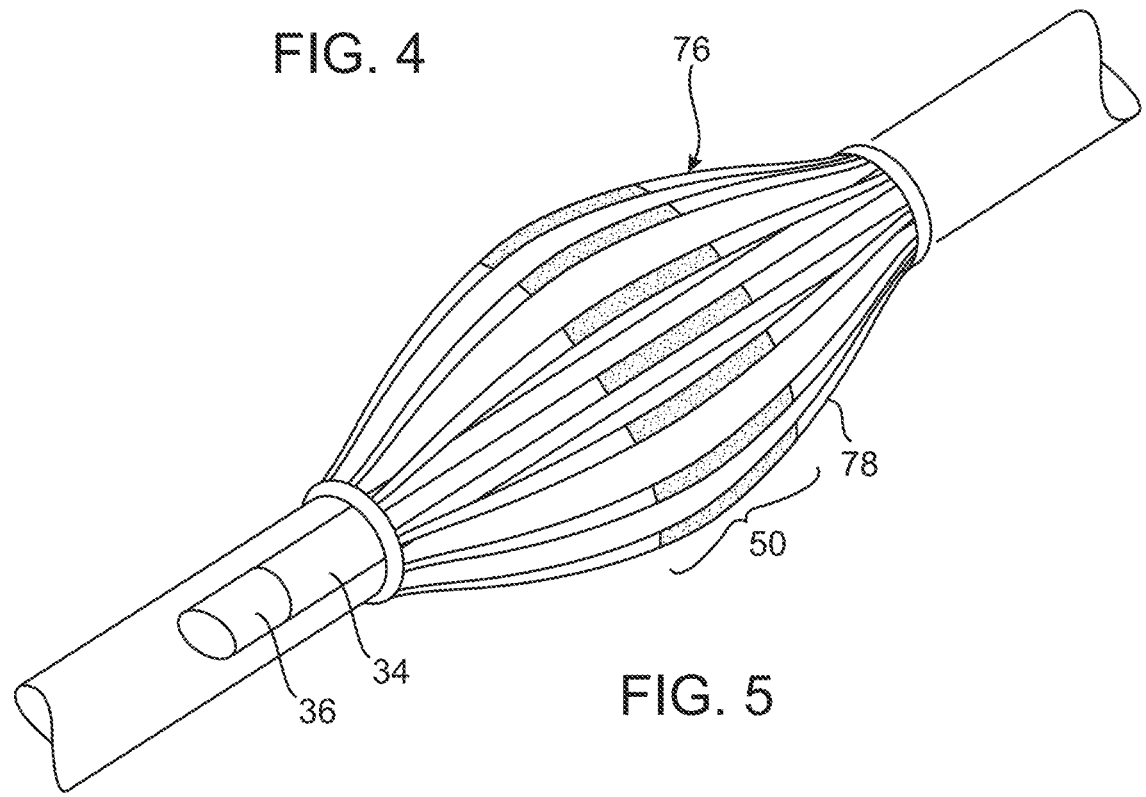
Figure 6A:
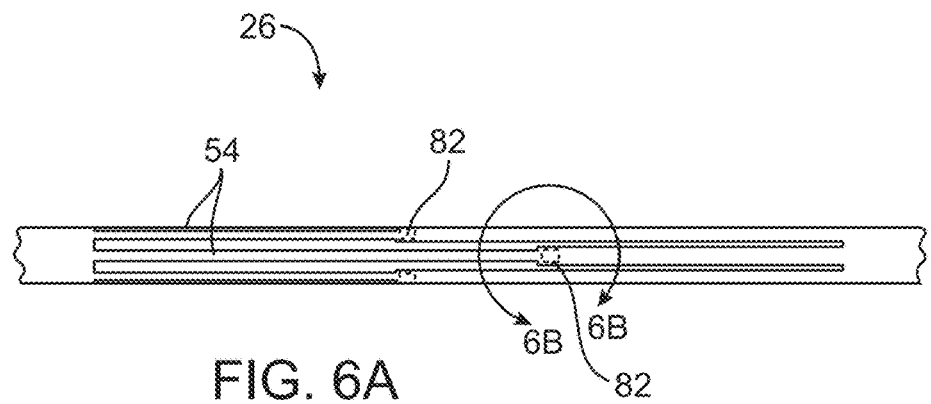
FIGS. 6A and 6B illustrate an exemplary basket structure having alternating axially offset electrodes in a circumferential array.

Referring now to FIGS. 4 and 6A, alternative embodiments may use different expandable structures in the form of different baskets. In FIG. 4, a braided basket 70 includes electrodes 50 mounted on braided structures 72. While metallic braided structures may be used in some embodiments with attention to electrical isolation of the electrodes, shorting of crossing metallic braided structures may be problematic. Hence, braided members 72 may comprise a high-temperature polymer or non-conductive material such as polyimide. An elongate electrode basket 76 may include electrodes 50 formed, for example, by selectively exposing a metallic surface along a central portion of basket member 78, while the remainder of the basket element is electrically isolated using a high-temperature polymer or the like so that the basket struts may be used as a conductor for energizing the electrode. Radial expansion of basket 76 is also illustrated by movement 71 of inner catheter body 58 relative to body 14. Expansion may also be effected by withdrawing a sleeve from over the basket, a pull wire, or the like. An intravascular ultrasound image sensor 36 of imaging catheter 34 is illustrated in FIG. 5 distal of expandable structures 76, with a proximal portion of the imaging catheter removed for clarity. Still further alternative expandable structures may be employed, including systems in which an array of electrodes is mounted circumferentially about a balloon, which may reduce blood contamination in the ablation area. Alternatively, a controlled ablation environment may be maintained with barriers proximally and/or distally of the expandable member by axially offset balloons, with an optional aspiration port again being disposed between such proximal and distal barriers.

Figure 6B:
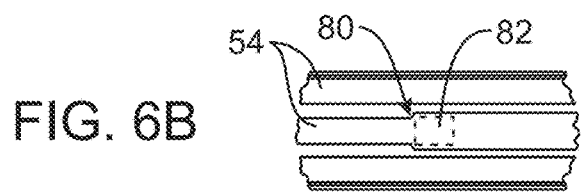

An exemplary expandable structure 26 is formed by cutting slots in a superelastic alloy tube such as a nickel titanium alloy or Nitinol™ tube. As can be understood with reference to FIG. 6B, expandable structures 54 may have circumferential widths 80 which are enhanced adjacent an electrode and/or electrode mounting location 82. As can be seen in FIG. 6A, the localized enhancement of the width 80 adjacent electrode mounting pads 82 may be axially offset, as described above. The slots forming expandable members 54, and hence the expandable members themselves may, for example, be 0.8 inches in length, with the expandable members having a circumferential width of about 0.25 inches.

Figure 7A:
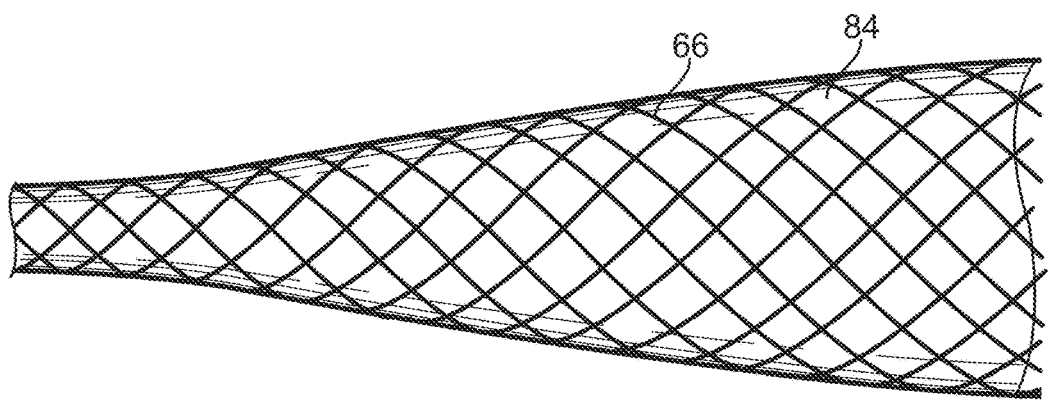
FIGS. 7A and 7B illustrate an exemplary ablation debris barrier for use with a basket.
Figure 7B:
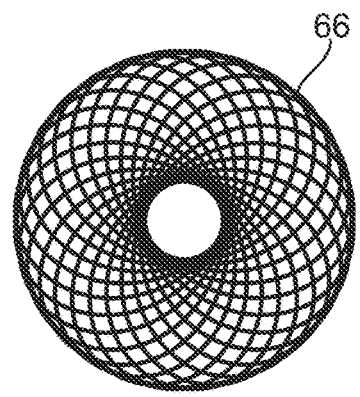
Figure 7C:
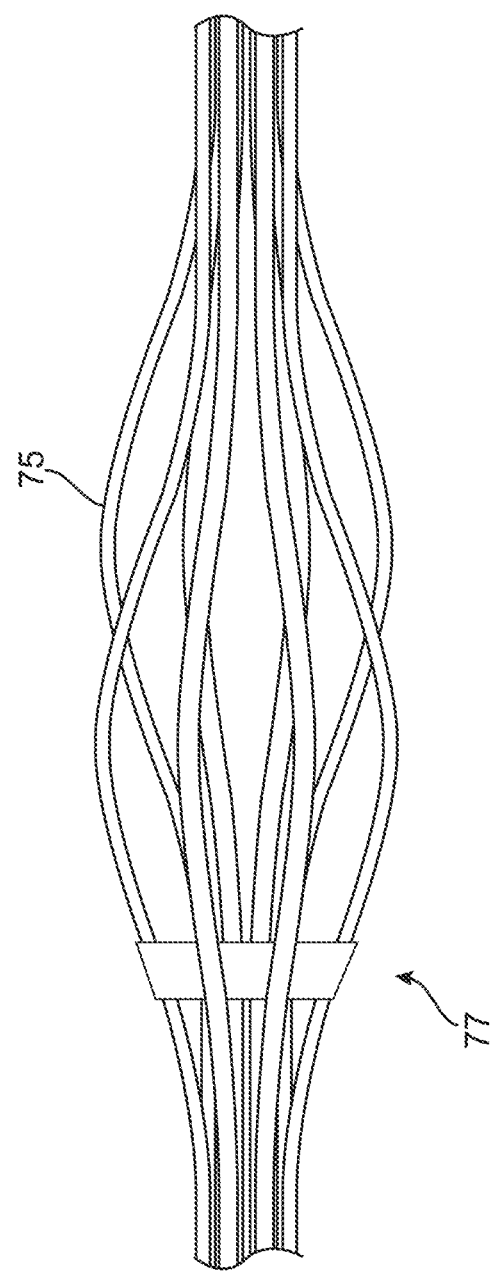
FIG. 7C illustrates an alternative basket and debris barrier.

Referring now to FIGS. 7A and 7B, side and end views of an expandable barrier in the form of a collapsible cone can be seen. Barrier 66 here comprises a braided Nitinol™ wire 84 coated in silicone, for example, by dipping a braid of a superelastic alloy such as a Nitinol™ braid in liquid silicone and allowing it to harden. Such cones may then be mounted over the proximal and distal portions of the expandable structure. As noted above, a variety of alternative barrier membranes may be employed. FIG. 7C illustrates a basket 75 with an integral barrier 77 coated directly on the basket. Barrier 77 comprises a polyurethane, which may be quite tear resistant. Alternative barrier membranes may comprise other materials such as PTFE or the like.

Figure 8:
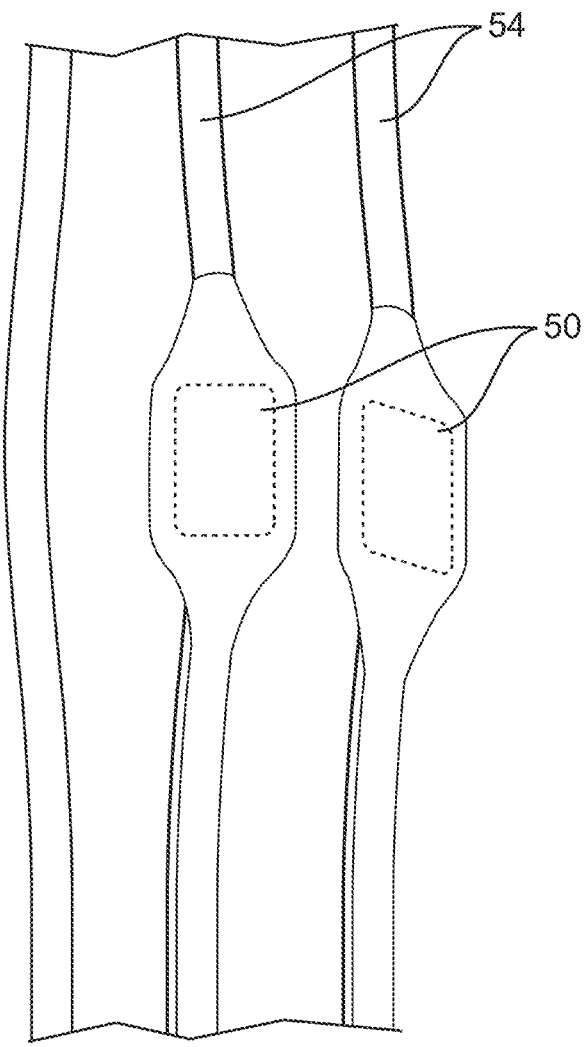
FIG. 8 illustrates electrodes having dedicated conductors mounted to associated elements of a superelastic metal basket.
Figure 9:
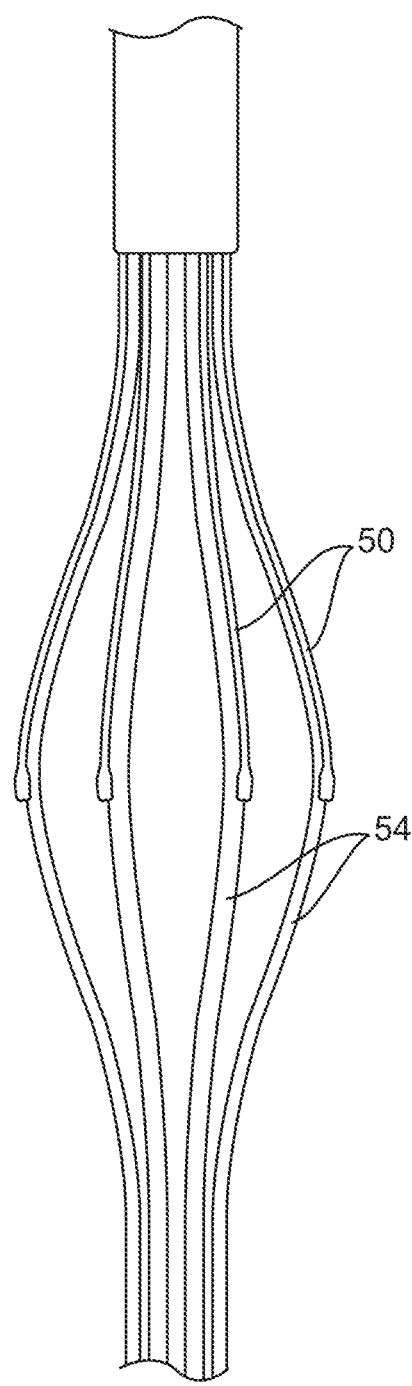
FIG. 9 is an illustration of a basket comprising polyimide supporting a circumferential array of electrodes.

Referring now to FIGS. 8 and 9, exemplary electrodes 50 supported by polyimide alloy expandable members 54 may be coated with a high-temperature polymer. Conductors 52 extend proximally from electrodes 50 as described above. High contrast radiopaque markers such as gold, platinum, platinum/iridium alloy, and the like may be attached to or near these struts. The markers could also be used as the electrodes.

Figure 10A:
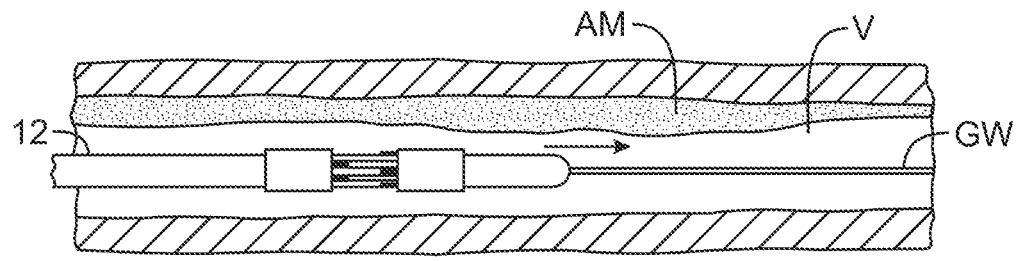
FIGS. 10A-E illustrate an exemplary atherosclerotic material remodeling and/or removal method using the catheter system of FIG. 2.

The use of catheter system 10 for remodeling and/or removal of eccentric atheroma from within a blood vessel can be understood with reference to FIGS. 10A through 10E. As seen in FIG. 10A, accessing of a treatment site will often involve advancing a guidewire GW within a blood vessel V at, and more often distally beyond a target region of atherosclerotic material AM. A wide variety of guidewires may be used. For accessing a vessel having a total occlusion, guidewire GW may comprise any commercially available guidewire suitable for crossing such a total occlusion, including the Safe-Cross™ RF system guidewire having forward-looking optical coherence reflectometry and RF ablation. Where atherosclerotic material AM does not result in total occlusion of the lumen, such capabilities need not be provided in guidewire GW, although other advantageous features may be provided. For example, guidewire GW may include a distal balloon to hold the guidewire in place and further inhibit movement of ablation debris and the like. Guidewire GW may be positioned under fluoroscopic (or other) imaging.

Figure 10B:
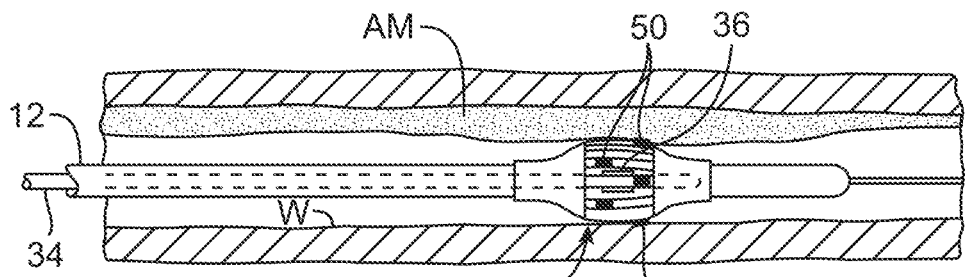

Catheter 12 is advanced distally over guidewire GW and positioned adjacent to atherosclerotic material AM, often toward a distal portion of the occlusion as can be understood with reference to FIGS. 10A and 10B. Expandable structure 26 expands radially within the lumen of the blood vessel so that electrodes 50 radially engage atherosclerotic material AM. Expandable structure 26 may be expanded by, for example, pulling a pullwire extending through catheter body 14 to the coupled (directly or indirectly) to distal portion 62 of expandable body 26 (see FIG. 3). Alternatively, an inner catheter body 58 may be moved proximally relative to outer catheter body 14, with the inner catheter again being coupled to the distal portion of the expandable body. Still further alternatives are possible, including withdrawing a sheath from around the expandable body and allowing the expandable body to flex radially outwardly. In at least some embodiments, whether actuated from the proximal end of catheter 12 or simply by releasing the expandable body, the structural members defining the expandable body may comprise elastic or superelastic materials treated to expand radially outwardly, such as by heat-setting a superelastic Nitinol™ metal, polyimide, or the like. In some embodiments, guidewire GW may be removed after the ablation catheter is positioned and/or the basket is expanded. As atherosclerotic material AM is distributed eccentrically about catheter 12, some of electrodes 50 directly engage a luminal wall W, as can be understood with reference to FIGS. 10B and 10C.

Figure 10C:
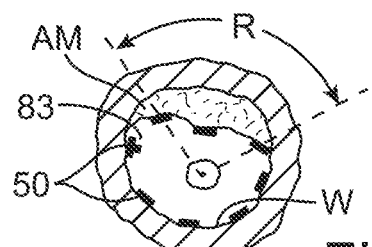

Imaging catheter 34 is positioned within a lumen of catheter 12 so that detector 42 extends to adjacent atherosclerotic material AM. The imaging catheter operates within and/or through catheter 12 so as to measure a thickness of atherosclerotic material concentrically about catheter 12 as illustrated in FIG. 10C with measurements often being taken at a plurality of axial locations so as to measure axial variation of the atherosclerotic material AM within the blood vessel, such measurements often progressing proximally. In many cases, atherosclerotic material AM will be distributed eccentrically within the vessel wall as shown in FIG. 10C. It should be noted that no portion of the vessel wall need be completely uncovered by atherosclerotic material for the measurement distribution to indicate that the obstruction is eccentric, as a relatively thin layer of atheroma along one portion or side of the blood vessel may be much different in thickness than a very thick layer of atherosclerotic material on an opposite side of the blood vessel V. In some methods, remodeling and/or ablation of all atheroma along one side may result in electrode/vessel wall engagement only after treatment begins.

In some cases, imaging catheter 34 may allow identification and/or characterization of atherosclerotic materials, plaques, tissues, lesions, and the like from within a blood vessel. For example, imaging catheter 34 may determine an axial and/or circumferential localization of a target plaque for treatment. Where treatments are intended for atherosclerotic plaques so as to enhance blood flow through the lumen, the treatment may be tailored to provide short term and/or long term increases in lumen diameter and blood flow. Where catheter 34 identifies a circumferentially and/or axially localized vulnerable plaque, that vulnerable plaque may be targeted for a suitable treatment to inhibit deleterious release of thrombolitic materials, often by thickening a fibrous cap of the vulnerable plaque, making the plaque less vulnerable to rupture, decreasing a size or danger of release from a lipid-rich pool of the vulnerable plaque, or the like. Hence, catheter 34 may be used to provide information similar to that available through histology so as to indicate a composition of an atheroma (by identifying and location, for example, a fibrous cap, smooth muscle cells, a lipid pool, calcifications, and the like.) Intravascular ultrasound catheters may now be capable of such atheroma characterizations, and these characterizations may also be provided by optical coherence tomography intravascular catheters, intravascular MRI antennas, and other catheter-based imaging systems, or by non-invasive imaging modalities such as MRI systems, and the like.

Suitable imaging catheters for use in the present catheter system are commercially available from a wide variety of manufacturers. Suitable technology and/or catheters may, for example, be commercially available from SciMed Life Systems and Jomed-Volcano Therapeutics (providers of intravascular ultrasound catheters), Light Lab™ Imaging (developing and commercializing optical coherence tomography catheters for intravascular imaging), Medtronic CardioRhythm, and the like. Still further alternative technologies may be used, including ultra fast magnetic resonance imaging (MRI), electrical impedance atheroma depth measurements, optical coherence reflectometry, and the like.

The systems, devices, and methods described herein may optionally make use of imaging techniques and/or atherosclerotic material detector devices which are at least in part (optionally being entirely) disposed outside of the body lumen, optionally being disposed outside of the patient body. Non-invasive imaging modalities which may be employed include X-ray or fluoroscopy systems, MRI systems, external ultrasound transducers, and the like. Optionally, external and/or intravascular atherosclerotic material detectors may also be used to provide temperature information. For example, a system having an MRI antenna may detect tissue temperatures such that a graphical indication of treatment penetration may be presented on the system display. Tissue temperature information may also be available from ultrasound and/or optical coherence tomography systems, and the temperature information may be used as feedback for directing ongoing treatments, for selecting tissues for treatment (for example, by identifying a hot or vulnerable plaque), and the like.

As with positioning of guidewire GW and advancement of catheter 12, positioning of sensor 30 of imaging catheter 34 may be facilitated by fluoroscopic or other imaging modalities. Location of sensor 36 relative to expandable structure 26 may be facilitated by radiopaque markers of catheter 34 adjacent sensor 36, and by the radiopaque structure (or corresponding radiopaque markers placed on or near) expandable structure 26, and/or by the use of radiopaque electrodes.

By expanding expandable structure 26 within blood vessel V, optional proximal and distal barriers 66, 68 (see FIG. 3) may form an at least partially, and preferably a substantially isolated environment within the blood vessel. That environment may be adapted to improve subsequent remodeling and/or ablation by aspirating blood from a port of aspiration lumen 22 disposed between proximal and distal barriers 66, 68, and by irrigating the isolated environment with a desired fluid, as described above. When provided, aspiration and/or irrigation may be performed, optionally simultaneously, so as to generate a flow within the controlled environment for removal of any vaporization gases, ablation debris, and the like.

Figure 10D:
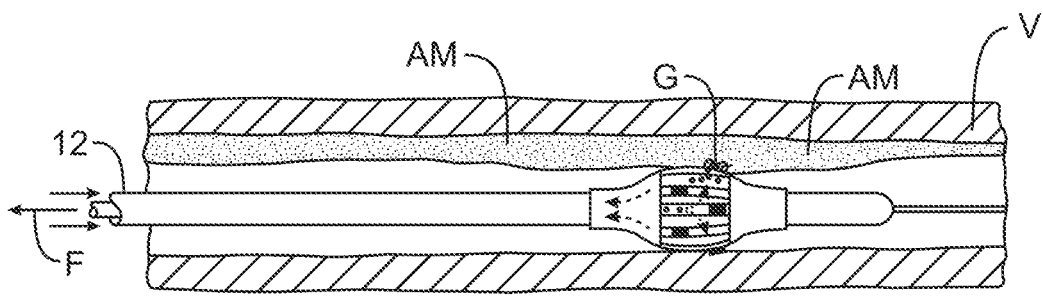

Referring now to FIGS. 10C and 10D, circumferential imaging often indicates that remodeling and/or ablation should be targeted to an eccentric portion or region R of the vessel wall W. To aid in registering the electrodes with the circumferential atheroma distribution, one strut of expandable structure 26 has an identifiable image, allowing the strut to serve as a rotational alignment key. Registering the electrodes may be achieved using intravascular imaging such as intravascular ultrasound (IVUS), optical coherence tomography ("OCT"), intravascular MRI, and/or the like, optionally using external imaging such as fluoroscopy, magnetic resonance imaging ("MRI"), or the like. Electronic registration may also be used. In response to this information, RF energy is directed to electrodes within region R. These actively energized electrodes define a subset of the overall array of electrodes, and selection of this subset of electrodes may be implemented using a controller as described hereinbelow.

The mechanisms of ablating atherosclerotic material within a blood vessel have been well described, including by Slager et al. in an article entitled, "*Vaporization of Atherosclerotic Plaque by Spark Erosion*" in *J. of Amer. Cardiol.* (June, 1985), on pp. 1382-6; and by Stephen M. Fry in "*Thermal and Disruptive Angioplasty: a Physician's Guide*;" Strategic Business Development, Inc., (1990) the full disclosures of which are incorporated herein by reference. Suitable vaporization methods and devices for adaptation and/or use in the present system may also be described in U.S. Pat. Nos. 5,098,431; 5,749,914; 5,454,809; 4,682, 596; and 6,582,423, among other references. The full disclosure of each of these references is incorporated herein by reference.

As illustrated in FIG. 10, energizing of selected electrodes 50 may result in vaporization of atherosclerotic material AM, so that the atherosclerotic material is removed from the blood vessel with an aspiration flow F through a lumen of catheter 12. A concurrent irrigation flow helps maintain the environment between the proximal and distal barriers of the catheter, and these two flows allow gases G and ablation debris to be entrained while inhibiting release of such emboli within blood vessel V. The fluid may also act as a cooling fluid to limit heating and collateral damage to other tissues, the circulating fluid often being at least less than body temperature, optionally being at or below room temperature.

Figure 10E:
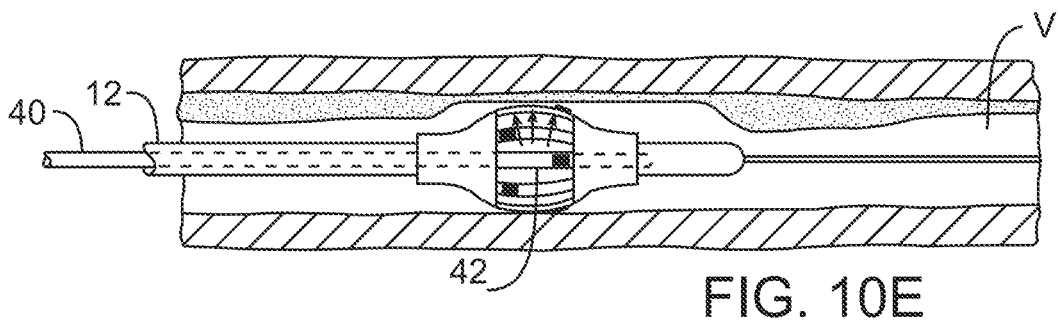

Referring now to FIG. 10E, as described above, it may not be necessary to completely remove all atheroma or atherosclerotic material from within the blood vessel. Providing an open lumen having an effective diameter of at least 80 or 85% of a nominal native lumen diameter may be sufficient. Remodeling treatments may provide acute effective open diameters in a range from about 30% to about 50%. In some embodiments, injury caused to the atherosclerotic material with the energized electrodes or other energy directing surfaces may result in subsequent resorption of the injured tissue lesions so as to provide further opening of the vessel after termination of treatment as part of the healing process.

To promote long term efficacy and inhibit restenosis of a treated region of blood vessel V, a restenosis inhibiting catheter 40 may be advanced through a lumen of catheter 12, so that a radiation source 42 irradiates the treated region of the blood vessel. Suitable intravascular radiation catheters are commercially available from Novoste™, Guidant, Johnson & Johnson, and the like. Restenosis inhibiting drugs similar to those now being employed on drug eluting stents may also be advanced through a lumen of catheter 12, optionally while the proximal and distal barriers again help to maintain a controlled environmental zone within the blood vessel, so that systemic drug delivery might be limited or avoided. In addition to known restenosis inhibiting drugs used on drug eluting stents, drugs which cause vasodilation might be employed. Known restenosis inhibiting drugs such as Rapamycin™ may also be used.

In some embodiments, expandable structure 26 may remain expanded against the vessel wall W and/or atherosclerotic material AM while catheter 12 moves within the blood vessel, the catheter often being drawn proximally during or between ablation treatments. Analogous movement of a radially expanded perforate basket is employed, for example, when measuring temperatures of blood vessels so as to detect vulnerable plaque in systems now being developed and/or commercialized by Volcano Therapeutics. Alternatively, the basket may be repeatedly contracted, axial movement of the catheter 12 employed to reposition the basket, with subsequent expansion of the basket at each of a plurality of treatment locations along atherosclerotic material AM. Repeated intravascular imaging or other atherosclerotic material thickness measurements circumferentially about catheter 12 may be employed, with the remodeling and/or ablation often being halted temporarily so as to allow an image to be acquired intermittently during an ablation procedure. A final image may be taken to verify remodeling and/or ablation has been successful.

Figure 14:
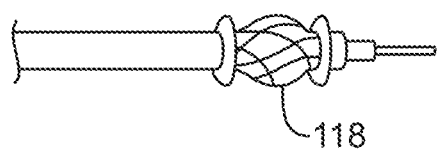

Referring now to FIGS. 11 through 21, a variety of alternative catheter structures are schematically illustrated, with many of these structures providing a microenvironment or controlled environmental zone within the blood vessel which has been enhanced for remodeling and/or ablation. A variety of emboli inhibiting barriers are also described and/or illustrated, including silastic balloons, flexible lips, or expandable cones which may be axially offset from the ablation electrodes. For example, referring to FIGS. 11 and 12, a system similar to that illustrated in FIG. 2 may employ a remodeling and/or ablation sleeve 102 having a proximal hub 104 and receiving an imaging catheter and a guidewire GW in an axial lumen of the sheath. A microenvironment is provided by a microchamber lip 106, which may comprise silicon or the like. Bipolar electrodes 50 may (though need not necessarily) generate gas and/or other ablation debris, which the silicon lip may help to contain. A vacuum port 108 of hub 104 is in fluid communication with a vacuum port 110, while a saline fluid infusion port 112 together with a saline injection passage 114 may be used to control and/or modify the microenvironment for remodeling and/or ablation. As illustrated in FIG. 13, alternate microchambers may be effected using silicon-like lips 116 fully encircling the catheter sheath 102, dual balloons, or the like. As illustrated in FIG. 14, such structures may be combined with a basket 118 supporting RF electrodes so as to provide electrode contact within a microchamber. The basket may optionally comprise a Nitinol™ shaped memory alloy.

Figure 15:
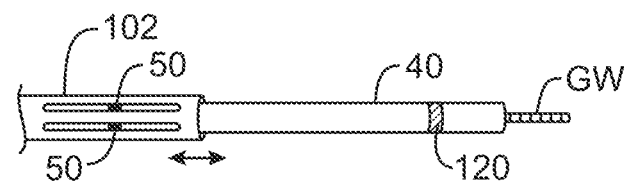

Referring now to FIG. 15, more generally, remodeling/ablation sleeve 102 may support electrode 50 for radiofrequency energy, and may provide one or more lumens for coaxial and/or biaxial insertion of an imaging catheter 34 (such as an IVUS catheter) and/or guidewire GW. Imaging catheter 34 may have a transducer in the form of an array 120.

Figure 16:
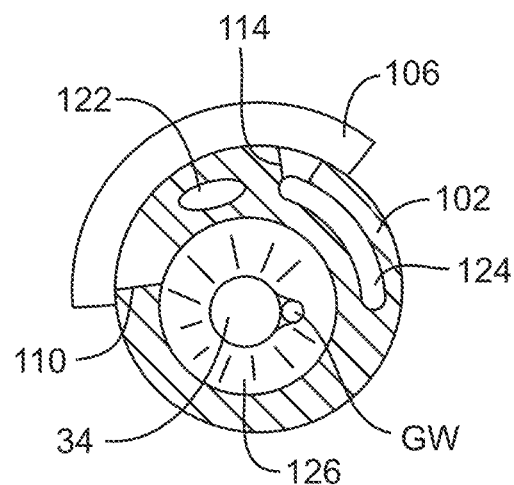

Referring now to FIG. 16, a remodeling/ablation sleeve 102 similar to that shown in FIGS. 11 and 12 has (here in cross section) has an electrode wire lumen 122, a saline injection lumen 124, and the opening of the vacuum port 110 to the working lumen of sheath 102 in which the imaging or IVUS catheter 34 and guidewire GW are disposed. A silicon lip or valve 126 allows a vacuum to be transferred to the microenvironment.

Figure 17:
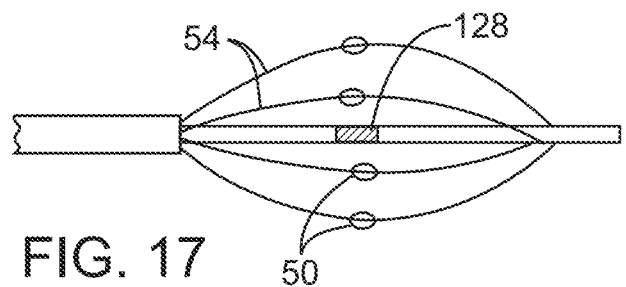
Figure 17A:
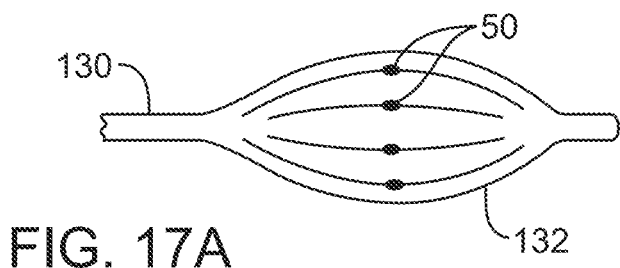

Still further alternative arrangements are illustrated in FIGS. 17 and 17A. In the embodiment of FIG. 17, an inner electrode 128 is used in a bipolar system along with outer electrodes 50, which contact the tissue for treatment. FIG. 17A schematically illustrates use of a balloon catheter 130 having a balloon 132 (such as a latex balloon). On the surface of the latex balloon electrodes 50 are mounted for use in selected pairs. Hence, a balloon (rather than a basket structure) may be used as a radially expandable structure for carrying the electrodes or other energy delivery surfaces.

Figure 18:
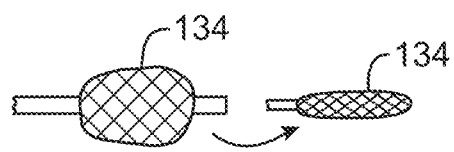
Figure 19:
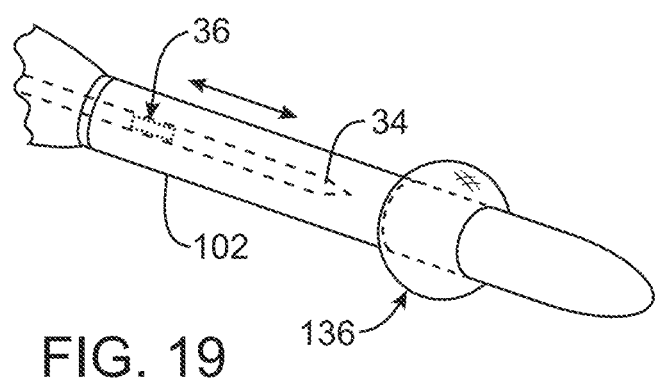
Figure 20:
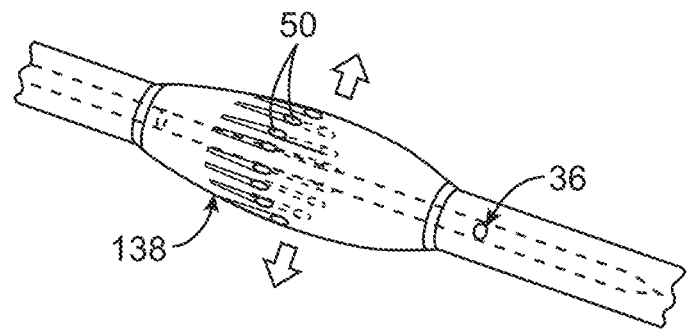
Figure 21:
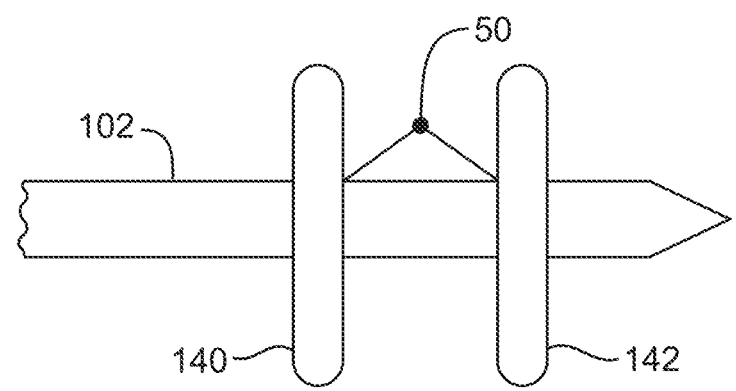

FIG. 18 schematically illustrates an expandable basket 134 being contracted from a large configuration to a small configuration. The basket may optionally be used as a cutting basket by providing appropriate edges, and/or may capture emboli within. FIG. 19 illustrates a remodeling/ablation sleeve 102 in which imaging catheter 34 travels axially back and forth to image, and in which a silastic balloon 135 is disposed distal of the treatment debris for emboli capture. FIG. 20 illustrates an alternate electrode delivery balloon 138 similar to balloon 132 of FIG. 17A, and illustrates electrodes 50 having flexible lumen extensions extending proximally therefrom. FIG. 21 schematically illustrates an RF electrode within a microchamber provided by proximal and distal barriers 140, 142 of sheath 102, in which a position of electrode 50 is actuated in the microchamber.

Figure 22:
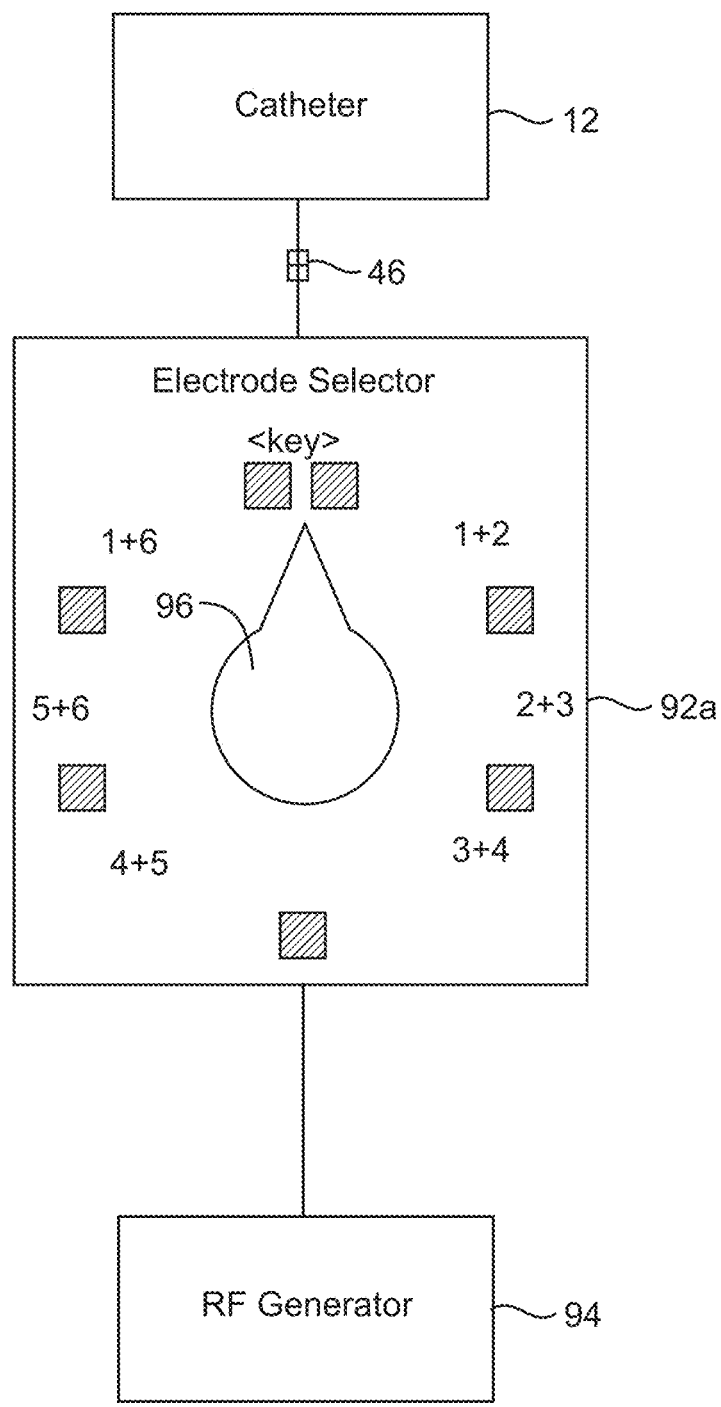
FIGS. 22-25 schematically illustrate controllers for selectively energizing electrodes in the system of FIG. 2.
Figure 23:
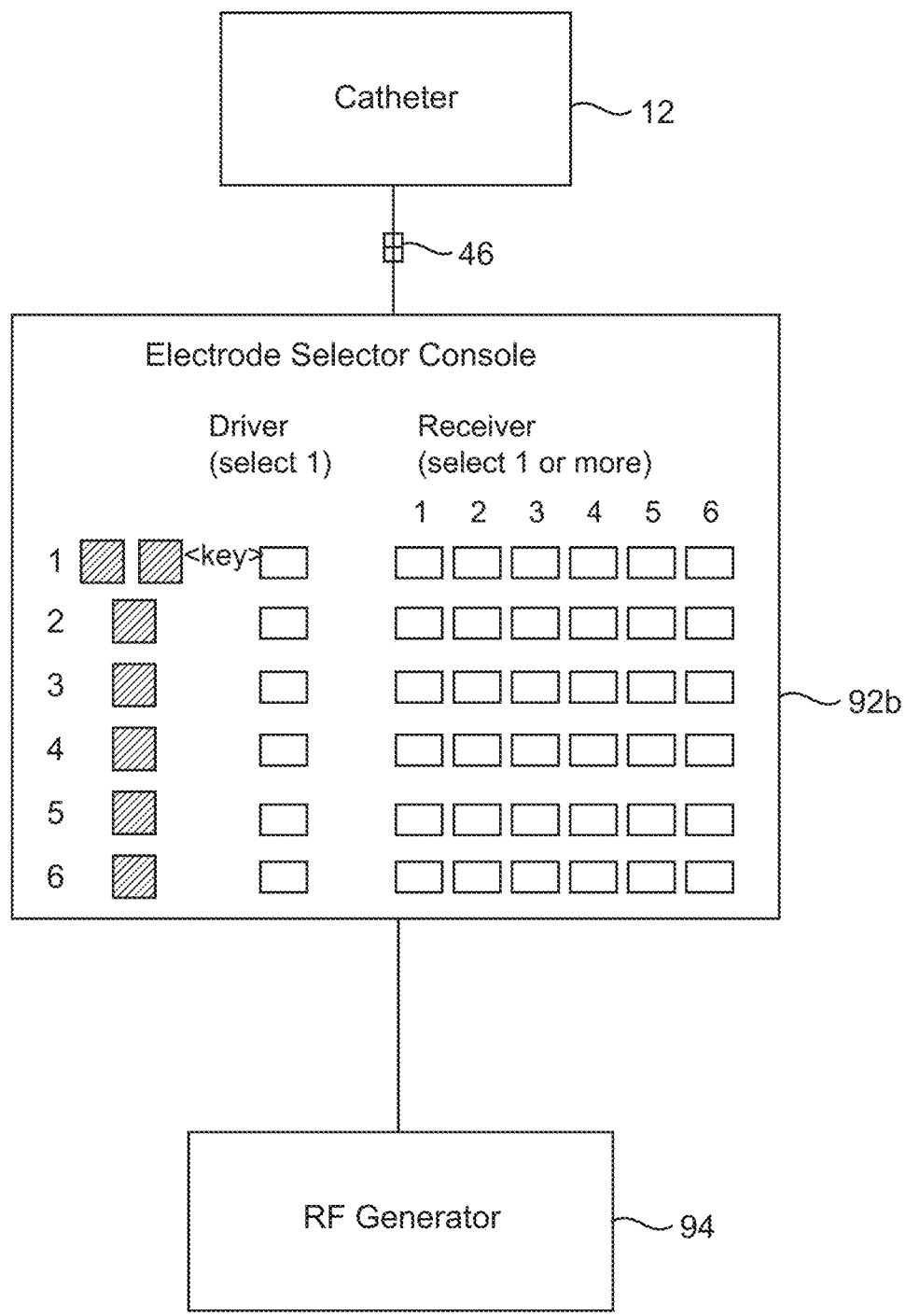
Figure 24:
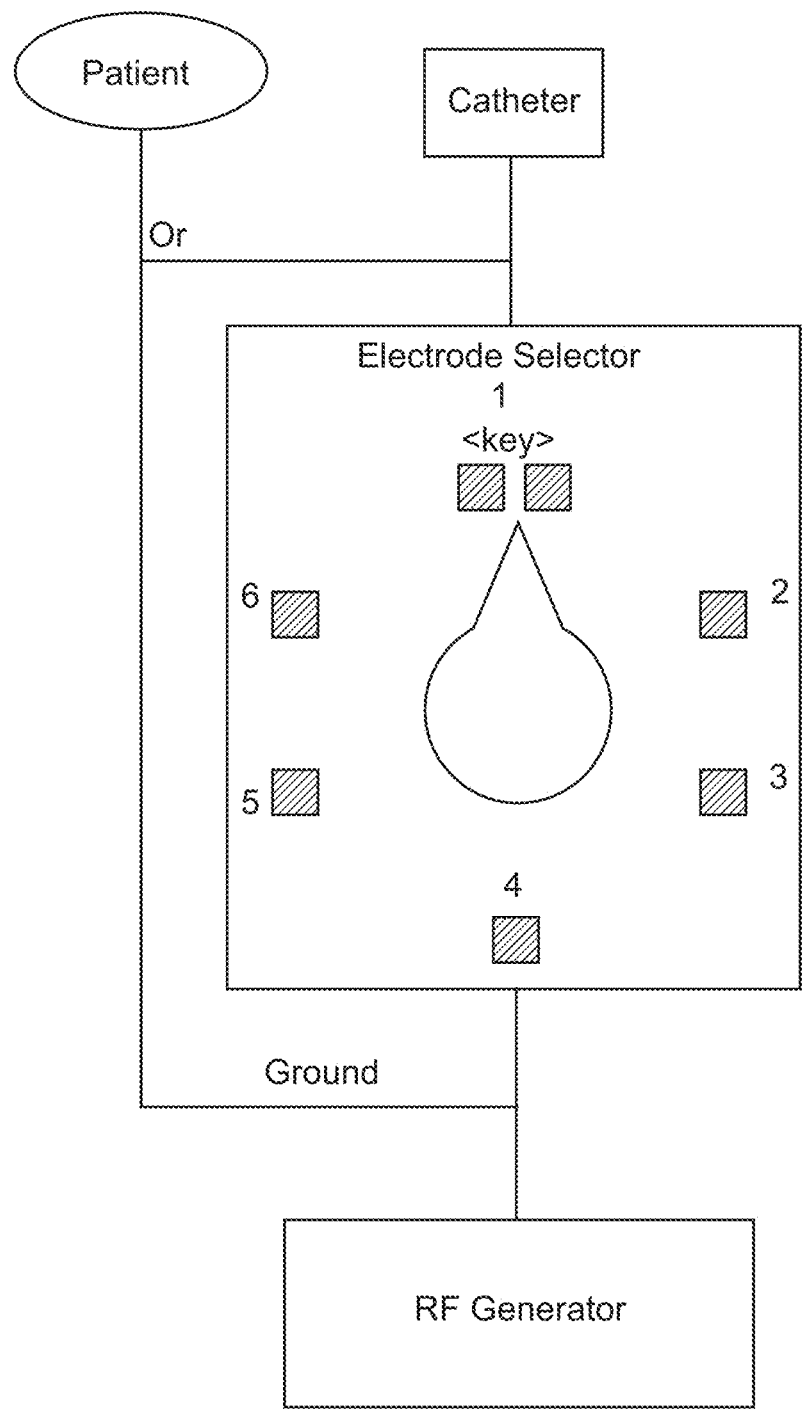
Figure 25:
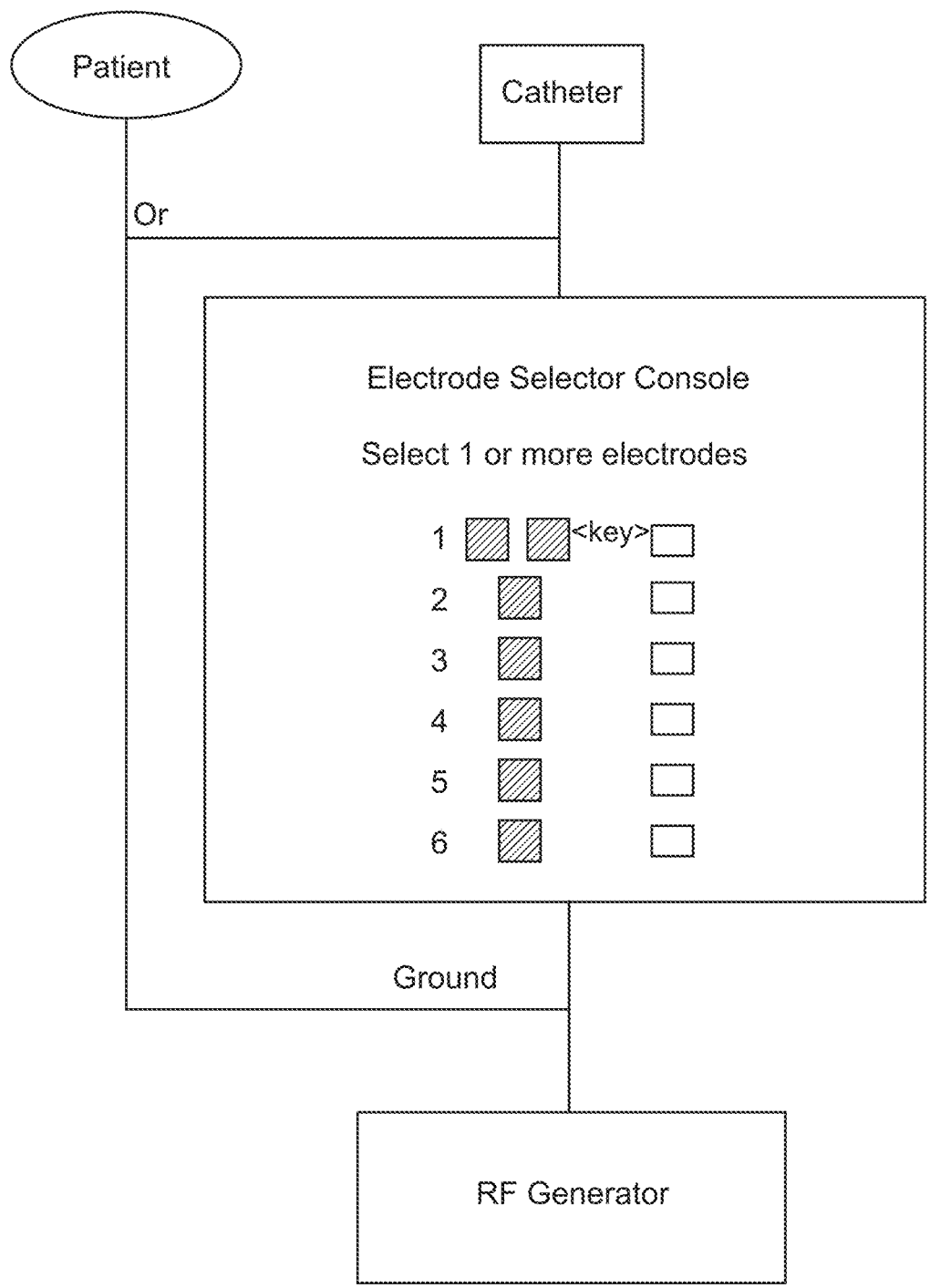

Referring now to FIGS. 22 and 23, alternative controllers 92a, 92b selectively energize electrodes of catheter 12 with RF power supplied from an RF generator 94. A wide range of RF energy types may be employed, including burst of 500 Khz, different types of waveforms, and the like. In controller 92a, a simple dial 96 is turned to point to a desired electrode pair to be energized. A "key" electrode may be registered with the intravascular imaging system, either electronically or by providing an electrode, electrode support member, or attached marker which presents a distinct image on the intravascular imaging display. This simplifies selection of one or more eccentric electrode pair along atheroma. Advantageously, catheter 12 need not be rotated into a proper orientation to accurately remodel and/or ablate the desired eccentric atherosclerotic material. Controller 92b includes similar capabilities, but allows the operator to select multiple electrodes for driving bipolar RF energy therebetween, providing greater flexibility in allowing multiple electrodes to be simultaneously energized. FIGS. 23 and 24 illustrate monopoly control arrangements similar to those of FIGS. 21 and 22, respectively. Patient grounding may be effected by a patient grounding plate, a ring electrode 2 to 5 cm proximal to basket 26, or the like. Once again, no catheter rotation is required to orient an active side of the catheter adjacent to the targeted atheroma since various eccentric ablation orientations can be selected through the electrode selection controller.

Figure 26:
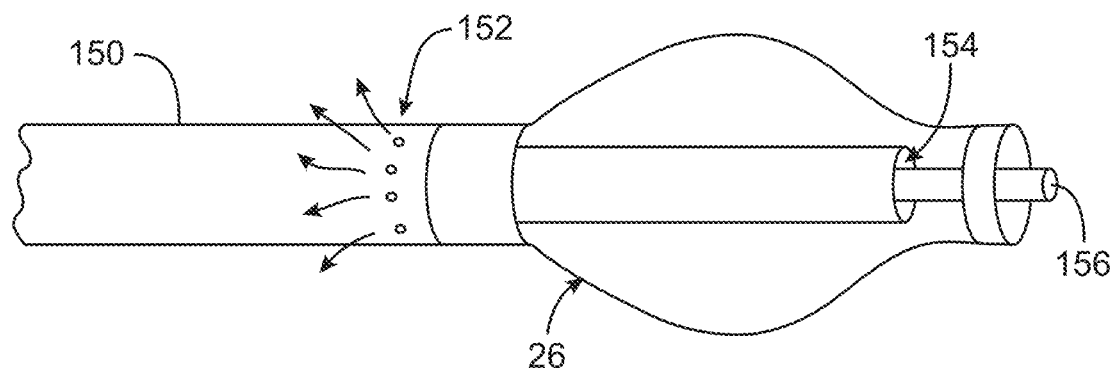
FIGS. 26 and 27 schematically illustrate alternative fluid flow paths for use in an atherosclerotic material remodeling catheter.
Figure 27:
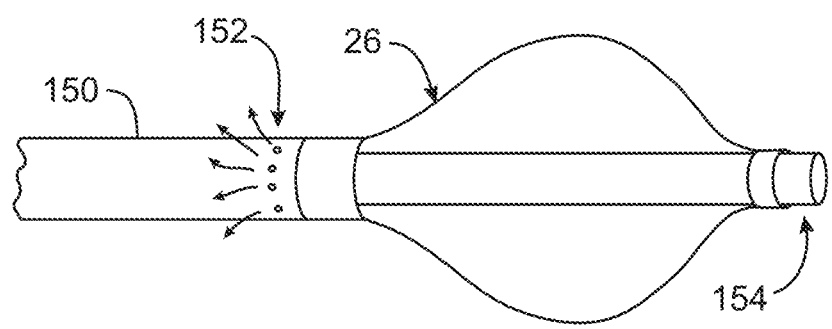

FIGS. 26 and 27 schematically illustrate alternative fluid flow arrangements for use in the catheters and methods described herein. In the embodiment of FIG. 26, a tubular body 150 extending proximally from expandable body 26 includes one or more irrigation ports 152, the irrigation ports here being disposed proximally of the expandable body. An aspiration port 154 contains a tubular body defining a guidewire and/or imaging catheter lumen 156. Irrigation fluid may flow distally, which may also be the direction of blood flow in the body lumen. Irrigation fluid may be aspirated through the aspiration port. In the embodiment of FIG. 27, lumen 154 is used for aspiration and for a guidewire and/or imaging catheter.

An alternative controller is illustrated in FIGS. 28A-D. This controller allows an operator to choose, for each electrode, whether to keep that electrode inactive, electrically couple that electrode to a first pole (sometimes referred to as pole A) of an energy source (such as an RF generator or the like), or to electrically couple that electrode to a second pole or pole B of the energy source. This controller allows a wide range of energized electrode configurations, including pseudo-monopolar modes where all electrodes except one are connected to one pole of the energy source (pole A) and one electrode is connected to the other pole (pole B). As can be understood with reference to FIG. 28A, controller 160 allows testing of many electrode configurations for RF remodeling and/or ablation, particularly those involving two or more electrodes. A switch panel 162 is shown in more detail in FIG. 28B. Each electrode (in this embodiment, up to eight electrodes) is electrically coupled to a 3-way switch numbered from 1 to 8, a switch disposed in the middle position indicates the electrode is not coupled to either pole, while a switch pushed toward the plus sign indicates the associated electrode is coupled to a red RF connector with the controller. Similarly, a switch pushed toward the minus sign indicates the associated electrode is electrically coupled to a black RF connector of the control box.

Figure 28A:
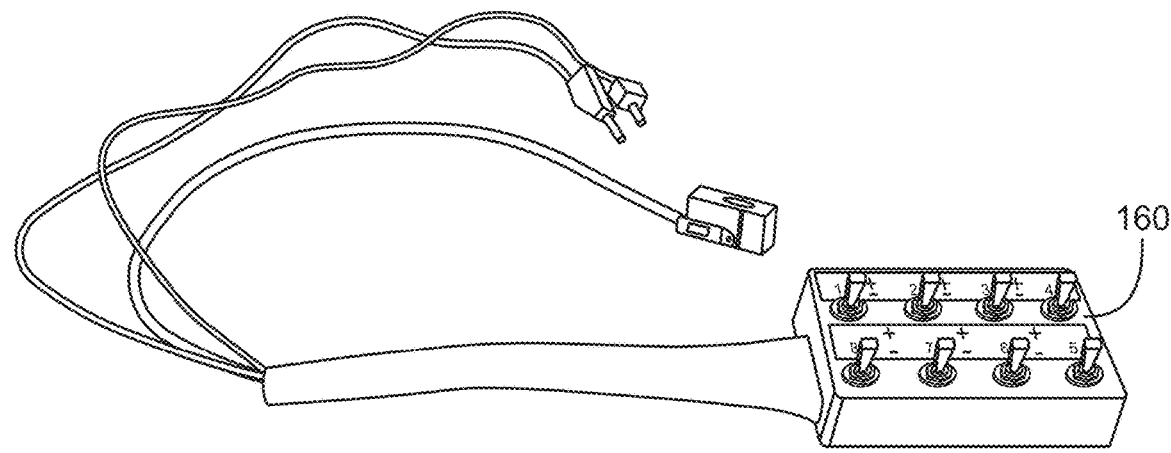
FIGS. 28A-28D illustrate an alternative controller for selectively energizing electrodes in the system of FIG. 2.
Figure 28B:
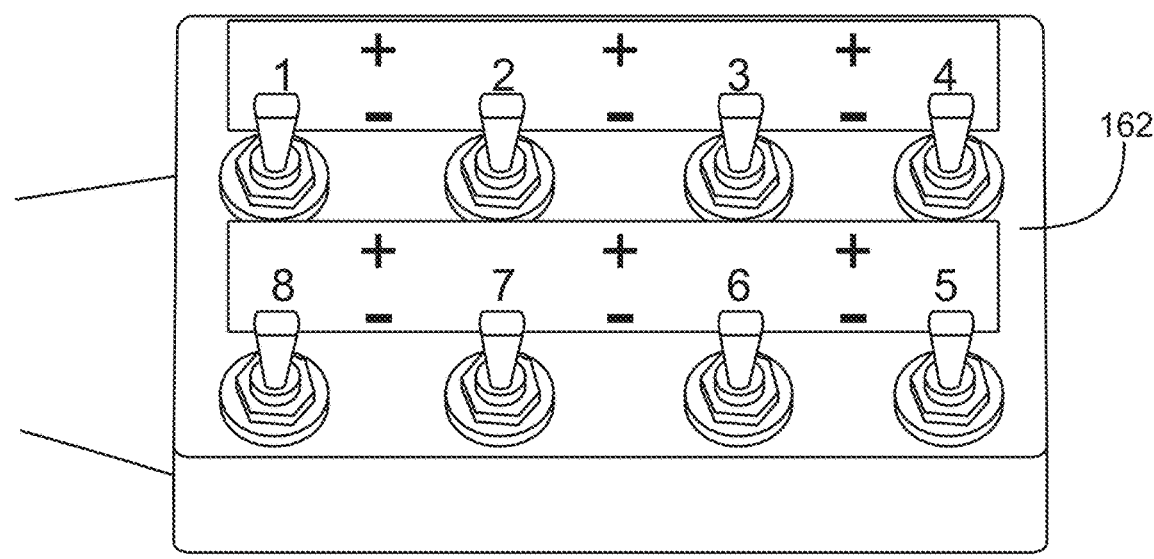
Figure 28C:
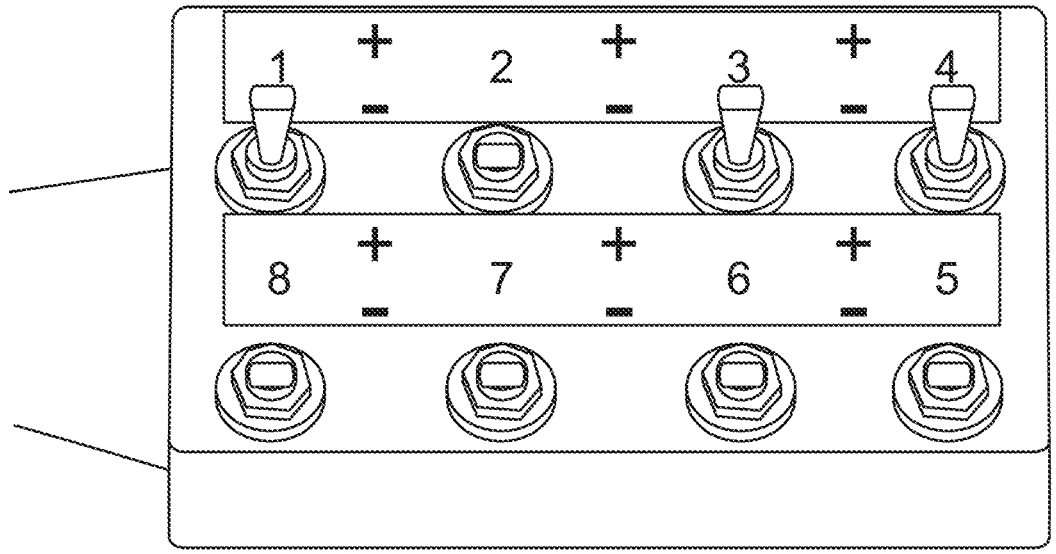
Figure 28D:
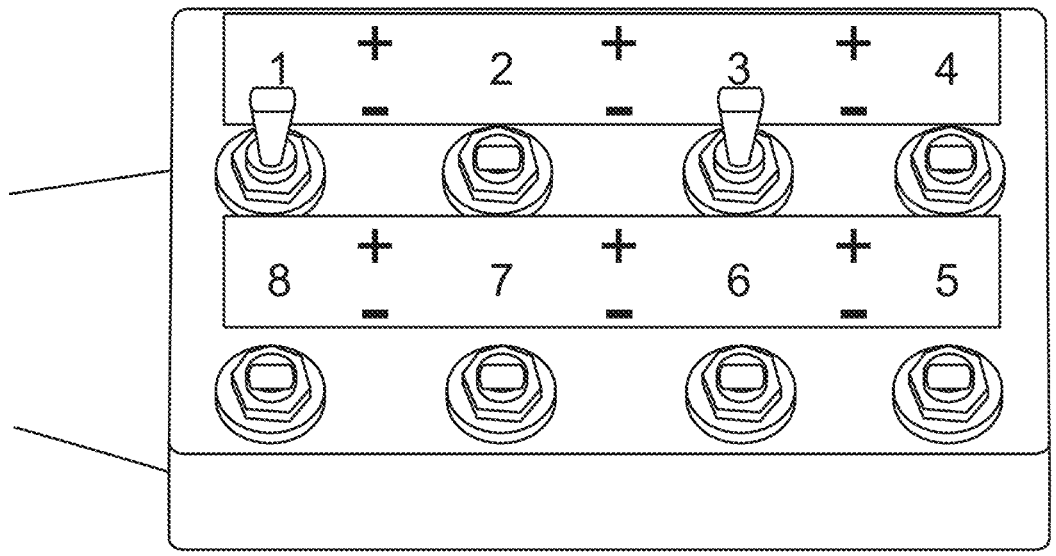

As can be understood with reference to 28C, electrodes associates with switches 3-8 are not coupled to either pole, electrode 1 is connected to the red RF connector, and electrode 2 is connected to the black RF connector. Activation of the RF generator will circulate bipolar RF energy between electrodes 1 and 2. In FIG. 28D, electrodes 5-8 are not energized, while electrodes 1 and 3 are coupled to the red RF connector. Electrodes 2 and 4 are connected to the black RF connector, so that activation of the RF generator will circulate bipolar RF energy between electrodes 1 and 3 and between electrodes 2 and 4.

Figure 29A:
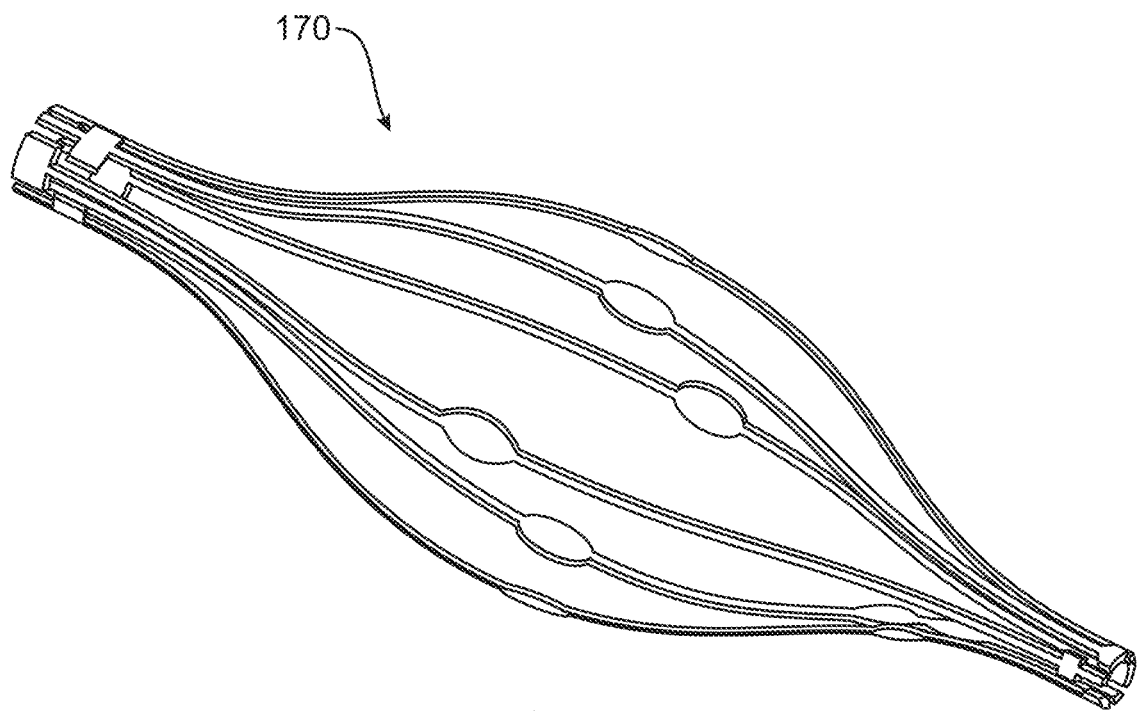
FIGS. 29A-29H illustrate an alternative basket structure formed with independent struts having a localized enhanced width for use as an electrode surface, along with components thereof.
Figure 29B:
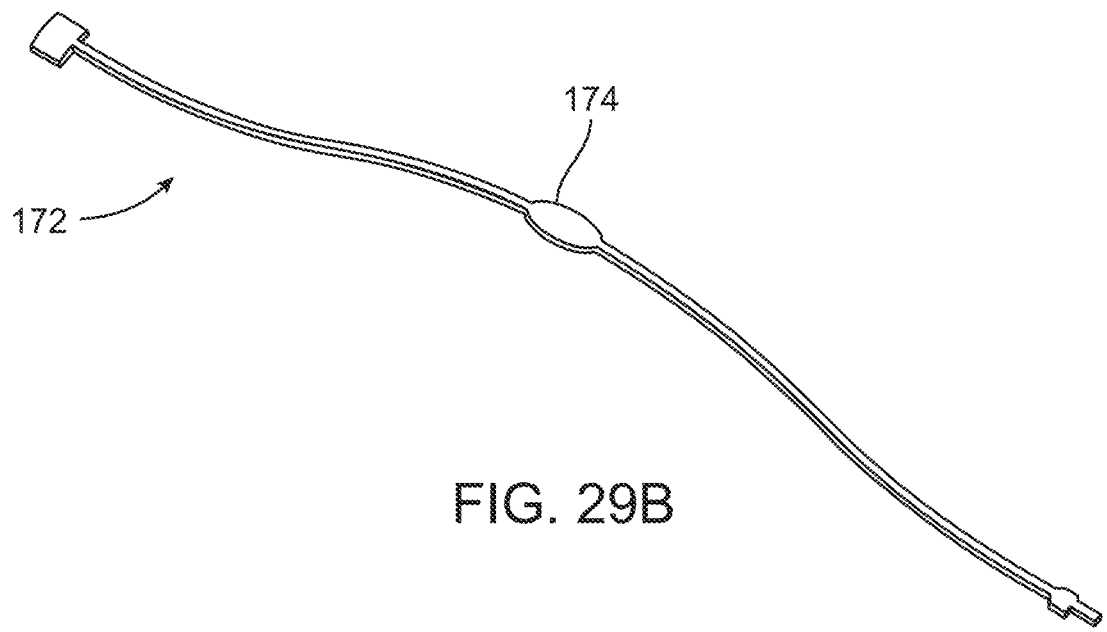
Figure 29C:
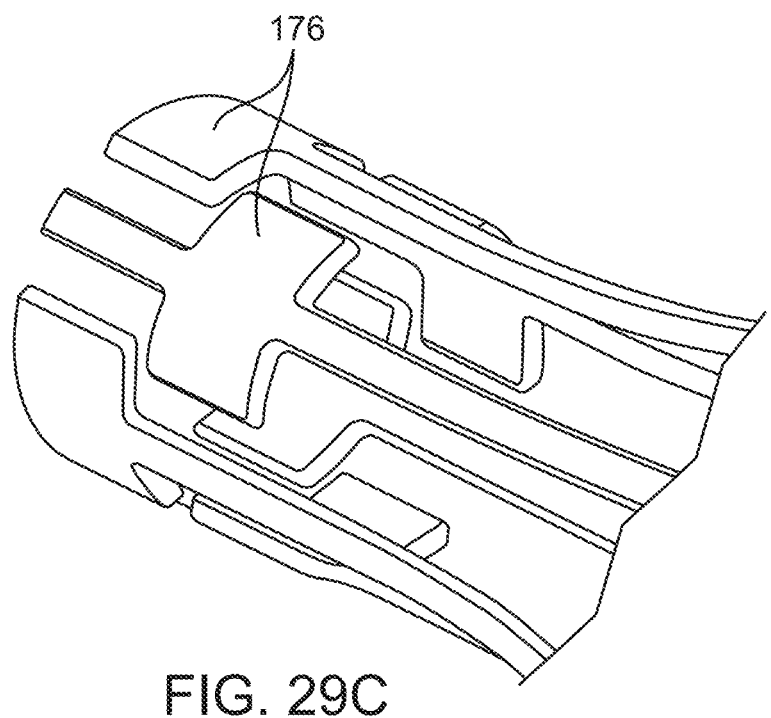
Figure 29D:
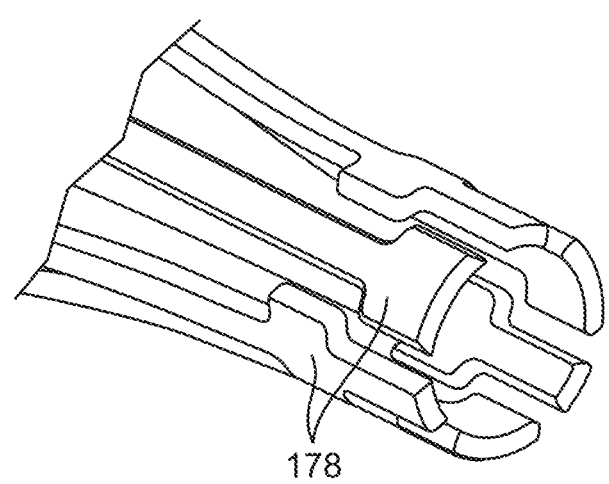
Figure 29E:
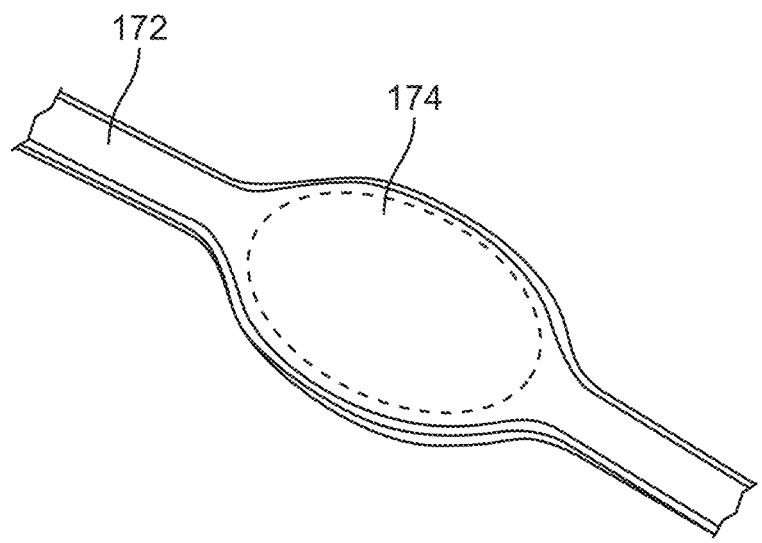

An exemplary self-expandable basket is illustrated in FIGS. 29A-29H. As can be understood from these drawings, electrodes may be fabricated as part of the struts 172 from which the basket is formed, for example, using a radially outwardly oriented surface of a localized widening 174 of each strut disposed in axially central portion of the strut, as can be seen in FIGS. 29B and 29E. Each arm may be formed from one piece of material, optionally comprising a Nitinol™ nickel-titanium shaped memory alloy, with the struts optionally being laser cut from a Nitinol™ tube. The electrode/basket may be, for example, coated with a high temperature polymer such as a polyimide. Electrodes 174 may be formed by inhibiting coating or removing coating from the desired portion of the associated strut 172 (as illustrated in FIG. 29E) so that the electrode surface is exposed for contact with atherosclerotic material. The struts may be separated from each other and structurally supported with an insulated material such as ultraviolet ("UV") cure or heat shrink sleeve, a polyethylene, Nylon™, or the like to form basket 170.

Figure 29F:
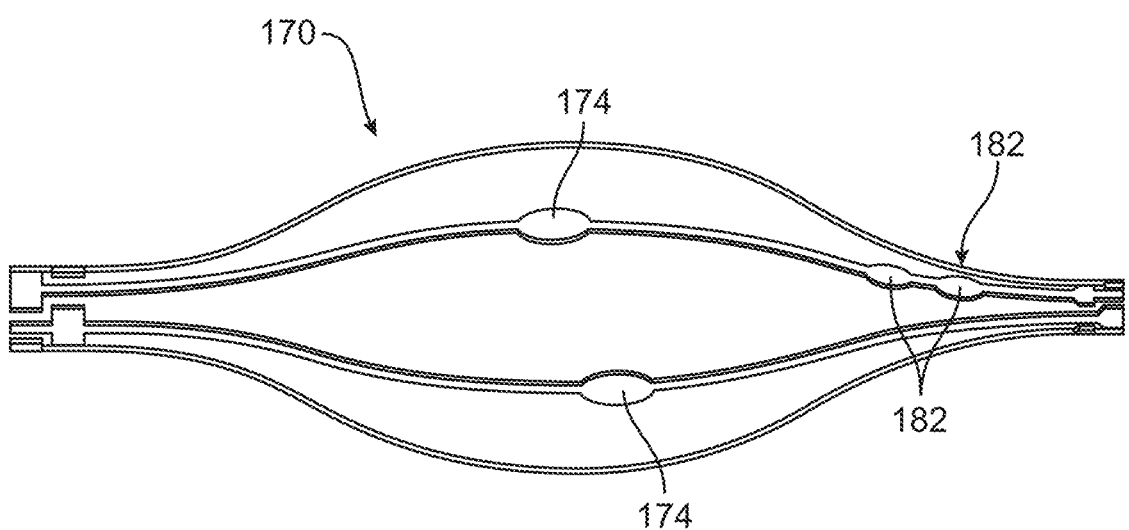

Each strut 172 may be used to conduct energy between electrode surface 174 and an electrical conductor extending proximally from the strut toward a controller. Proximal pads for connecting such conductors are illustrated in FIG. 29C, while distal structural pads 178 are illustrated in FIG. 29D. Adjacent electrodes 174 may be axially offset or staggered as can be seen in FIG. 29F. Insulating coating along each strut 172 may be inhibited or removed from an inner surface of proximal pads 176 so as to facilitate connecting of an associated conductive wire, such as by spot welding or the like. Alternative insulating materials may also be used, including parylene coatings, while alternative methods for attaching struts 172 to a catheter body may be employed, including adhesive bonding using insulating UV cure, embedding the pad structures in polyethylene, and the like.

Figure 29G:
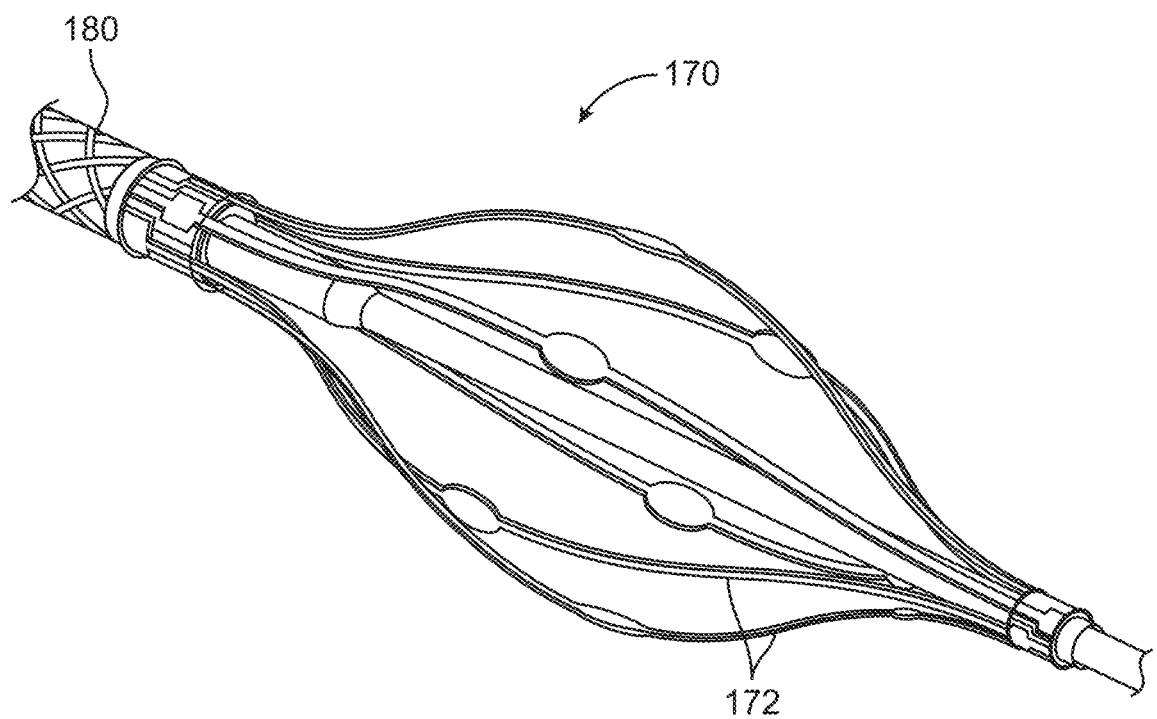

Exemplary structures for fixing struts 172 of basket 170 to a catheter body 180 are illustrated in FIG. 29G.

Figure 29H:
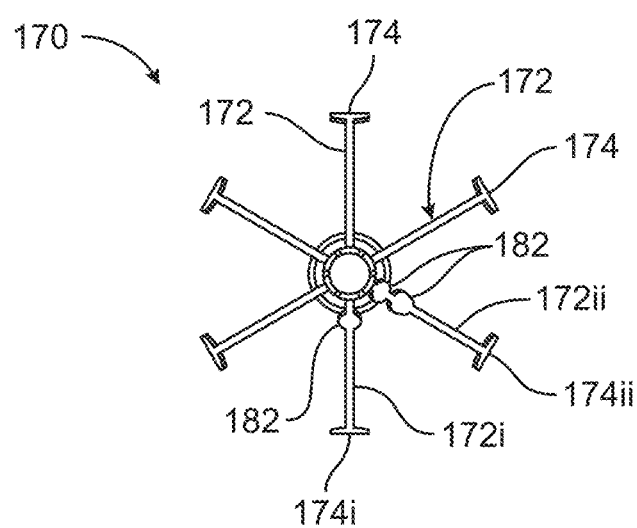

Referring now to FIGS. 29F and 29H, an alternative indicia providing a distinguishable image for rotationally registering selected electrodes 174 of basket 170 to images or other atherosclerotic material measurements can be understood. In this embodiment, an electrode 174i referenced as electrode 1 may have a radiopaque marker 182 disposed on the associated strut 172i. A strut 172ii supporting an associated second electrode 174ii may have two radiopaque markers 182 provide a circumferentially asymmetric count indicator allowing all electrodes to be referenced without ambiguity. The shape of electrodes 50 may vary, for example, electrodes 174 may be wider than other portions of struts 172 as illustrated in FIGS. 29A-G.

As described above, remodeling will often be performed using irrigation and/or aspiration flows. In many embodiments, an irrigation port directs fluid, such as a saline solution, from an irrigation lumen to an interior of the basket. An aspiration port may provide fluid communication between an aspiration lumen and an interior of the basket. One or both of these fluid flows may be driven continuously, or may alternatively pulsate before, during, and/or after treatment. In some embodiments, aspiration and/or irrigation flow may occur acutely or concurrently so as to circulate between the irrigation port and the aspiration port. Optionally, the flow may carry ablation debris to the aspiration port, where the debris may be evacuated through the aspiration lumen. There may be coordination between the irrigation system and the aspiration system such that the irrigation fluid may remain confined in an area closely adjacent the basket so as to inhibit embolization of ablation debris when the basket is expanded within the blood vessel. Such coordination, for example, may inhibit distal movement of ablation debris, and/or may obviate any need for a distal and/or proximal barrier or membrane. In some embodiments, the circulation of fluid between an irrigation port and an aspiration port may create an effectively bloodless environment adjacent the electrodes to facilitate remodeling and/or ablation, imaging of atherosclerotic tissue, and the like.

Figure 30A:
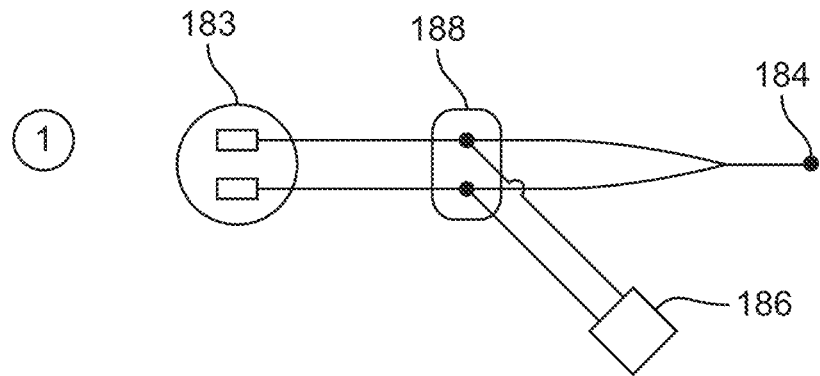
FIGS. 30A and 30B schematically illustrate electrical circuitry allowing thermocouples and other temperature sensors to be used both for measuring temperature and as electrodes.
Figure 30B:
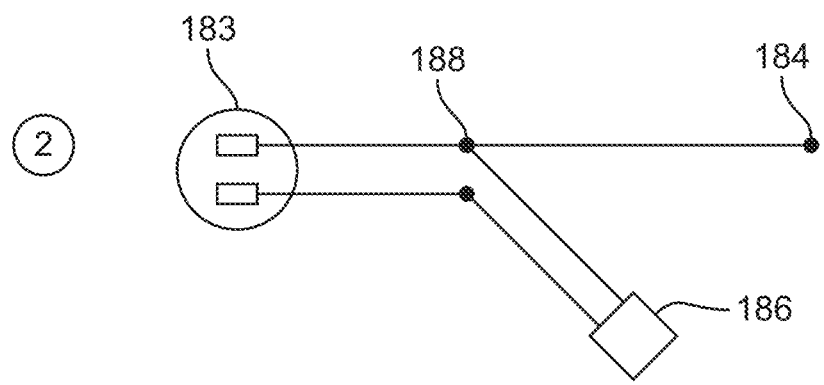

Referring now to FIGS. 30A and 30B, control of energy directed from the catheter systems and structures of the present invention may optionally make use of thermocouples and other temperature sensing structures. Thermocouples such as K-type thermocouples (+CH/−AL) may be attached to or near one or more struts of an expandable structure to provide temperature measurements. For example, such structures may provide tissue temperature measurements, blood temperature measurements, treatment temperature measurements, and/or the like.

Optionally, a temperature measurement structure may also be used as an RF electrode, for example, by employing one or more of the structures illustrated in FIGS. 30A and 30B. In the embodiment of FIG. 30A, a thermocouple 182 can be coupled to either an RF energy source 184 or a thermometer 186 by a switch 188. A similar embodiment is illustrated in FIG. 30B.

Figure 31:
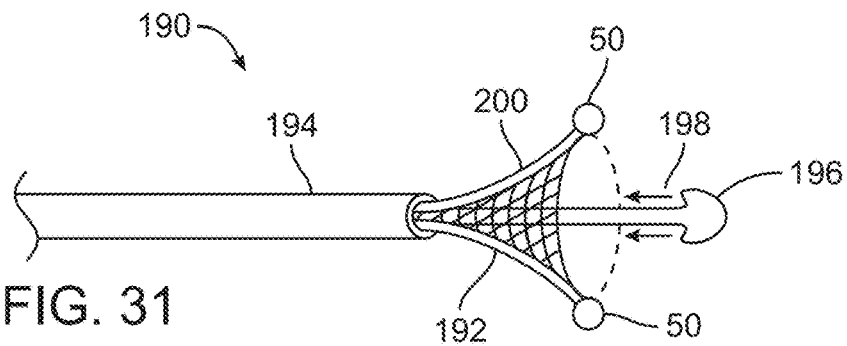
FIG. 31 schematically illustrates an alternative catheter structure for use in the methods described herein.

Referring now to FIG. 31, an alternative catheter system 190 includes a plurality of electrodes 50 supported by struts 192. Struts 192 expand radially when extended distally through a sheath 194 so that a circumferential array of the electrodes is collapsible. A ball-shaped tip 196 includes proximally oriented high pressure jets 198, and the ball-shaped tip may be used as one pole with selected electrodes 50 being used as the other pole. Alternatively, bipolar power may be driven between electrodes 50 or the like. Optionally, a proximal barrier 200 such as a screen may be used to inhibit movement and/or capture any debris.

When the RF electrodes are energized, the high pressure jets may also be activated so as to provide a saline flush. A venturi effect may entrain the debris for transport proximally through a catheter lumen for evacuation, typically using an aspiration source coupled to sheath 194. Debris may be trapped in barrier 200 which may comprise a screen, a solid sheet, a net, or the like. In some embodiments, low pressure jets may be used from adjacent ball tip 196 in place of high pressure jets.

Figure 32A:
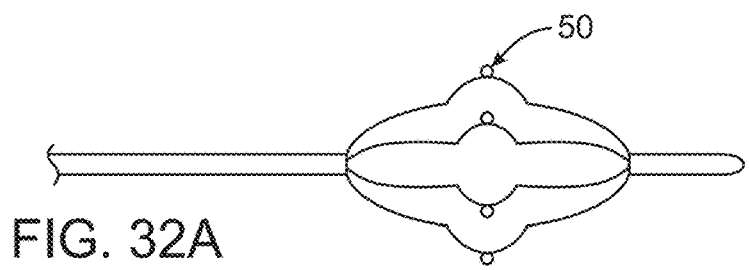
FIGS. 32A-32D schematically illustrate alternative basket and catheter structures for use in the methods described herein.
Figure 32B:
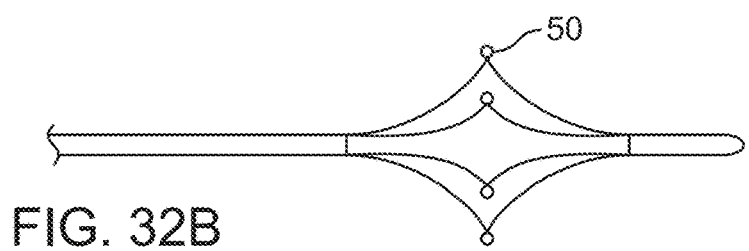
Figure 32C:
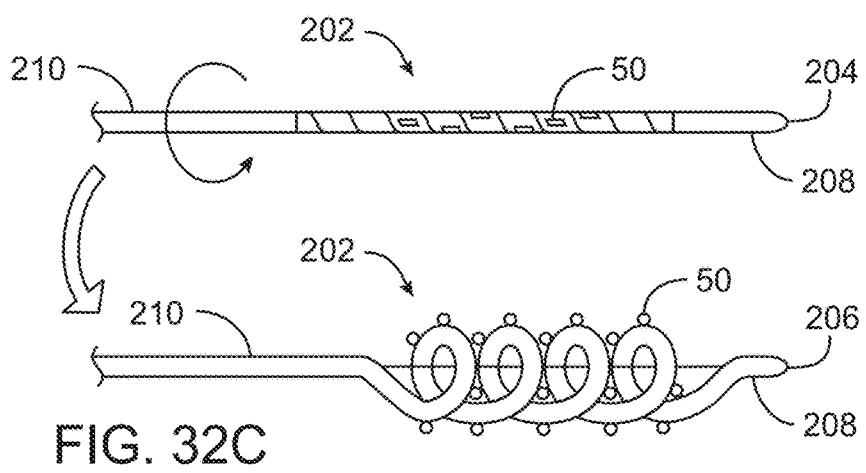
Figure 32D:
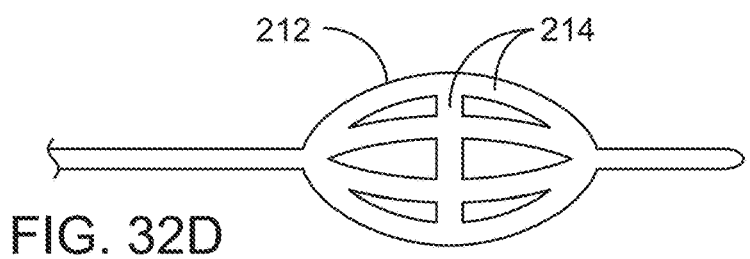

Referring now to FIGS. 32A-32D, alternative expandable structures may avoid kinking or flattening of the expandable structure when the expandable structure bends axially, such as when it is expanded along a bend in a body lumen. In the embodiment of FIG. 32C, a coil or helical expandable structure 202 has a small profile configuration 204 and a large profile configuration 206, and may be deployed and/or retracted by twisting a distal end 208 and/or a proximal tubular body 210 relative to each other, by a pull/release mechanism, or the like. Aspiration and/or irrigation may be provided through the proximal tubular member 210 as described above, and the coil structure may include a single loop or a plurality of loops so as to provide one or more circumferential rows of electrodes 50 when in the expanded configuration 206. In the embodiment of FIG. 32D, an inflatable expandable structure 212 includes axial struts and/or rings formed as tubular inflatable balloons so as to allow the expandable structure to expand from the small profile configuration to the shown large-profile configuration.

Figure 33:
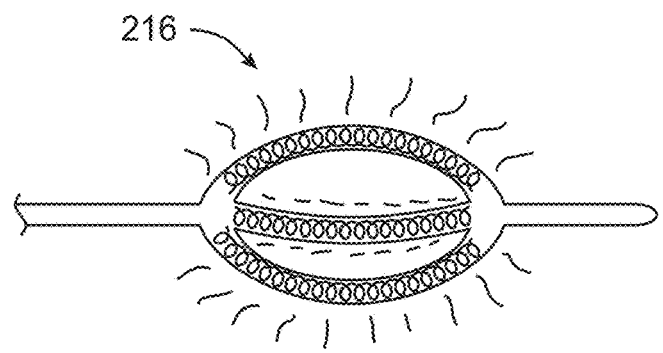
FIG. 33 schematically illustrates an alternative catheter structure using microwave energy to remodel atherosclerotic material.
Figure 34:
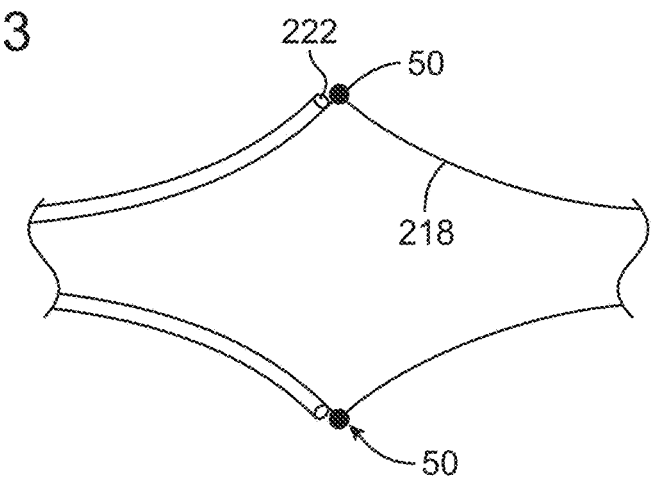
FIG. 34 schematically illustrates an alternative catheter structure having lumens extending toward the electrodes so as to provide directed irrigation flow in the methods described herein.
Figure 35:
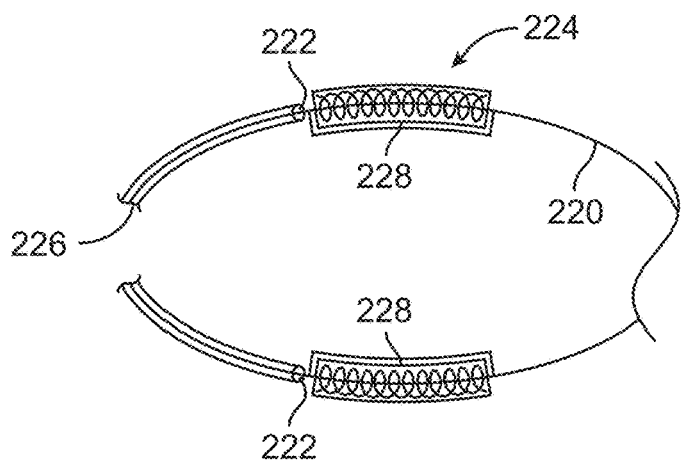
FIG. 35 schematically illustrates a further alternative catheter basket structure having lumens for directing irrigation flow toward the microwave antennas for use in the methods described herein.

Still further alternative expandable structures and energy delivery surfaces are schematically illustrate in FIGS. 33-35. In a microwave treatment device 216 illustrated in FIG. 33, each strut of a basket may include a helicoidal microwave antenna, with an inner side of the antenna shielded to avoid emitting energy toward the catheter axis. Alternative microwave antennas may also be employed, including unidirectional antennas which allow depth between an energy delivery surface and a target tissue to be varied by varying a focus of the antenna. Such focused microwave devices may include antennas that are rotatable about the catheter axis, axially moveable, and the like.

In the embodiments of FIGS. 34 and 35, catheter bodies again support a series of struts 218, 220 and also have a plurality of irrigation or flush lumens. The irrigation lumens within the catheter body are in fluid communication with tubular structures extending along the (and in some cases being integrated into the) struts, so that fluid flush ports 222 direct saline or other fluids towards electrodes 50 or microwave antennas 224. Electrosurgical power for the energy delivery surfaces may be transmitted using the strut structure, or wires 226 may extend along the strut to the energy delivery surfaces. In the embodiment of FIG. 35, shield 228 along an inner portion of a microwave antenna 224 can be seen, which may limit microwave energy directed toward an imaging catheter. For embodiments employing microwave antennas as energy delivery devices, only one antenna of the circumferential array may be energized at a time, so as to avoid interference between conductors along the catheter body.

Figure 36:
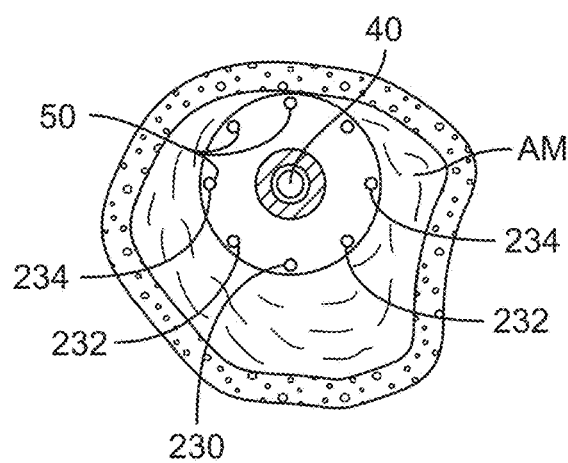
FIG. 36 is a schematic cross sectional view showing the application of different power levels through different electrodes so as to eccentrically remodel atherosclerotic materials.

Referring now to FIG. 36, controllers of the catheter systems described herein may allow distribution of differing power levels to differing pairs of electrodes. For example, in response to a circumferential distribution of atherosclerotic material AM such as that illustrated in FIG. 36, a controller may direct 50 watts of energy to a first electrode 230, 30 watts of energy to a pair of second electrodes 232 and only 10 watts of energy to a pair of third electrodes 234. Other electrodes may have no energy directed thereto, as described above. In some embodiments, a differing power directed to the differing electrodes may be provided by controlling the duty cycle, for example, with 50 watts being provided by energizing one or more electrode for 50% of the time, 30 watts being provided by energizing an electrode 30% of the time, and the like.

Figure 37A:
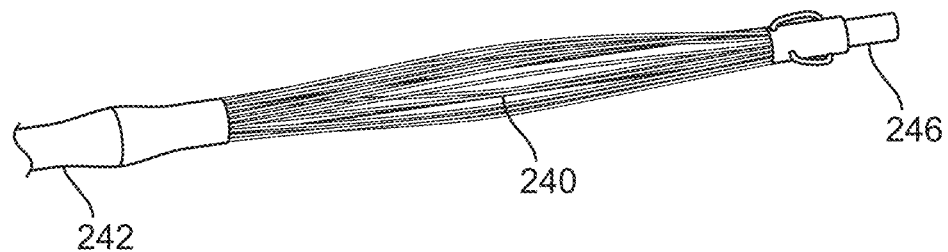
FIGS. 37A-37C illustrate a further alternative catheter basket structure, in which the basket comprises polyimide for supporting a circumferential array of electrodes and facilitating intravascular imaging.
Figure 37B:
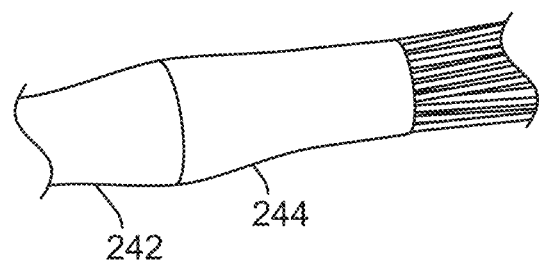
Figure 37C:
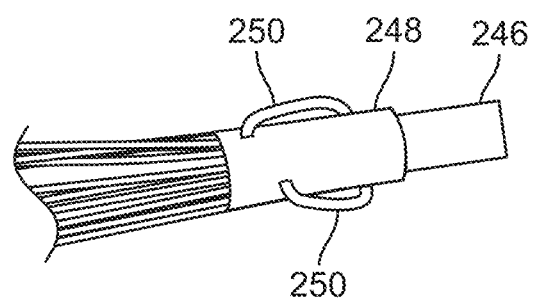

Referring now to FIGS. 37A-37C, many imaging modalities (including intravascular ultrasound, optical coherence tomography, intravascular MRI, and the like) may be at least in part blocked or degraded by positioning the image detecting structure within a metallic structure such as a basket formed of Nitinol™. Hence, there may be advantages in producing alternative expandable structures such as baskets comprising plastics or a polymer. In light of the heat generated by the electrodes of the systems described herein, it may be advantageous for such polymer basket structures 240 to comprise a high temperature polymer such as a polyimide. Alternative basket structures may comprise HDPE, PET, Nylon™, PEBAX™, and the like. As illustrated in FIG. 37B, proximal ends of the basket struts may be glued to a shaft 242 at a bond 244. An imaging catheter guide 246 may extend through a distal end of the basket structure 248, with the distal end of the basket free to slide axially along the guide. Pullwires 250 may be affixed to the distal end 248, so that pulling of the pullwires radially expands basket 240, with the pullwires running inside the proximal shaft 242. The basket may be retracted back to its small profile configuration by pushing of the pullwires, or the basket may include biasing means urging the basket to the small profile configuration. So as to avoid degradation to imaging performance, polymer tension members similar to fishing line may be used as pullwires. In the exemplary embodiment, the pole wires comprise Nitinol™ which has sufficient compressional rigidity to push the basket to its small profile configuration.

Basket 240 may be formed by cutting struts from a tube of the polymer material, with the distal portion 248 preferably remaining uncut. The proximal ends of the struts may be separated prior to forming bond 244, and ring-shaped RF electrodes may be slid along each arm and glued to the desired configuration along the intermediate portion of the basket.

Figure 38A:
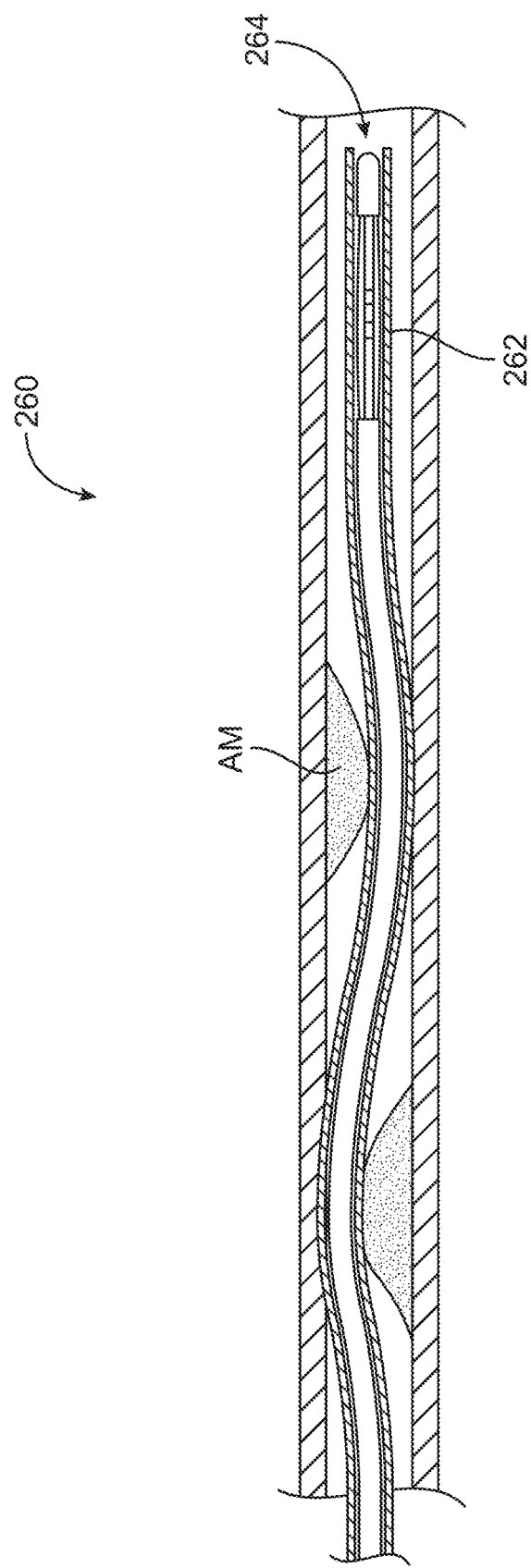
FIGS. 38A-38E are cross sectional side views through a body lumen showing additional aspects of treatment methods and devices described herein.
Figure 38B:
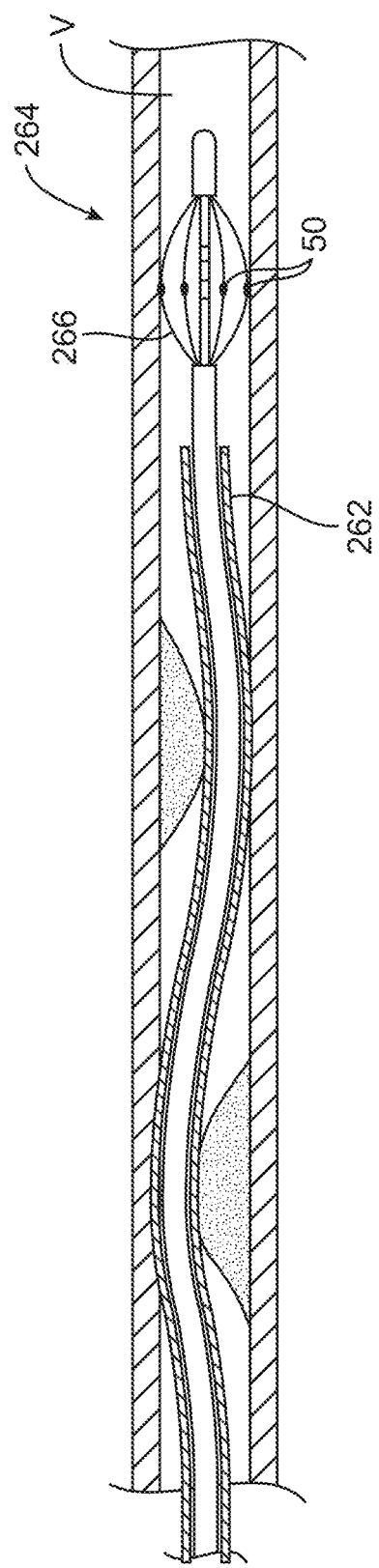

Exemplary treatment methods are illustrated in FIGS. 38A-38H. In FIG. 38A, the catheter system 260 includes a basket covering sheath 262 over an atherosclerotic material detecting and treating catheter 264 as described above. In this embodiment, outer basket sheath 262 radially restrains the basket 266, which is biased to expand radially when released from the outer sheath, as illustrated in FIG. 38B. In some embodiments, the basket may be expanded after the outer sleeve is retracted, such as by pulling pullwires, rotating one portion of the catheter relative to the other, or the like. Regardless, as the basket expands within the vessel V, electrodes 50 of the basket engage the surrounding vessel wall. An imaging transducer near basket 266 of an imaging catheter disposed in a lumen of the treatment catheter evaluates the vessel V, and the detection/treatment catheter system 264 is pulled proximally along the artery or vessel V.

Figure 38C:
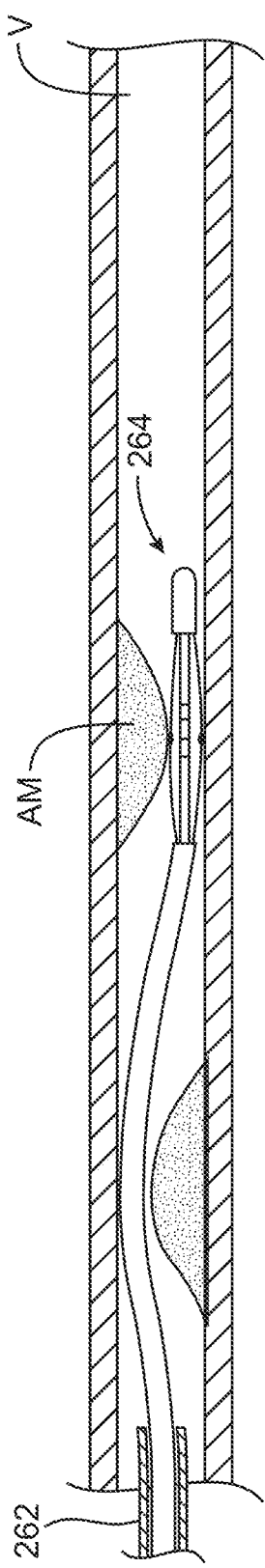
Figure 38D:
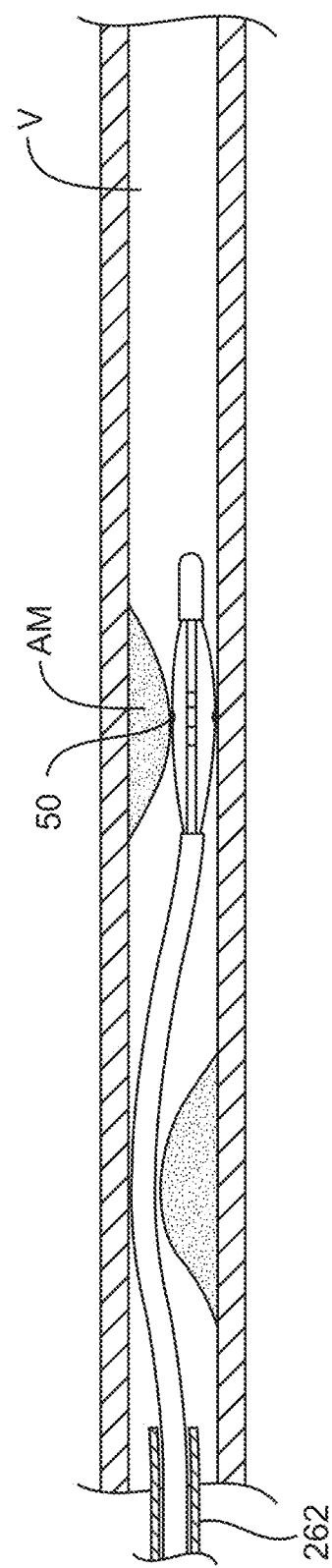
Figure 38E:
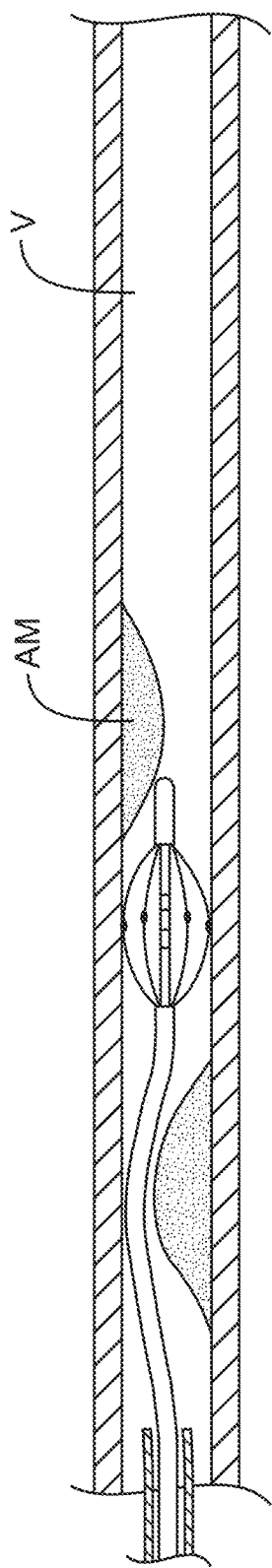
Figure 38F:
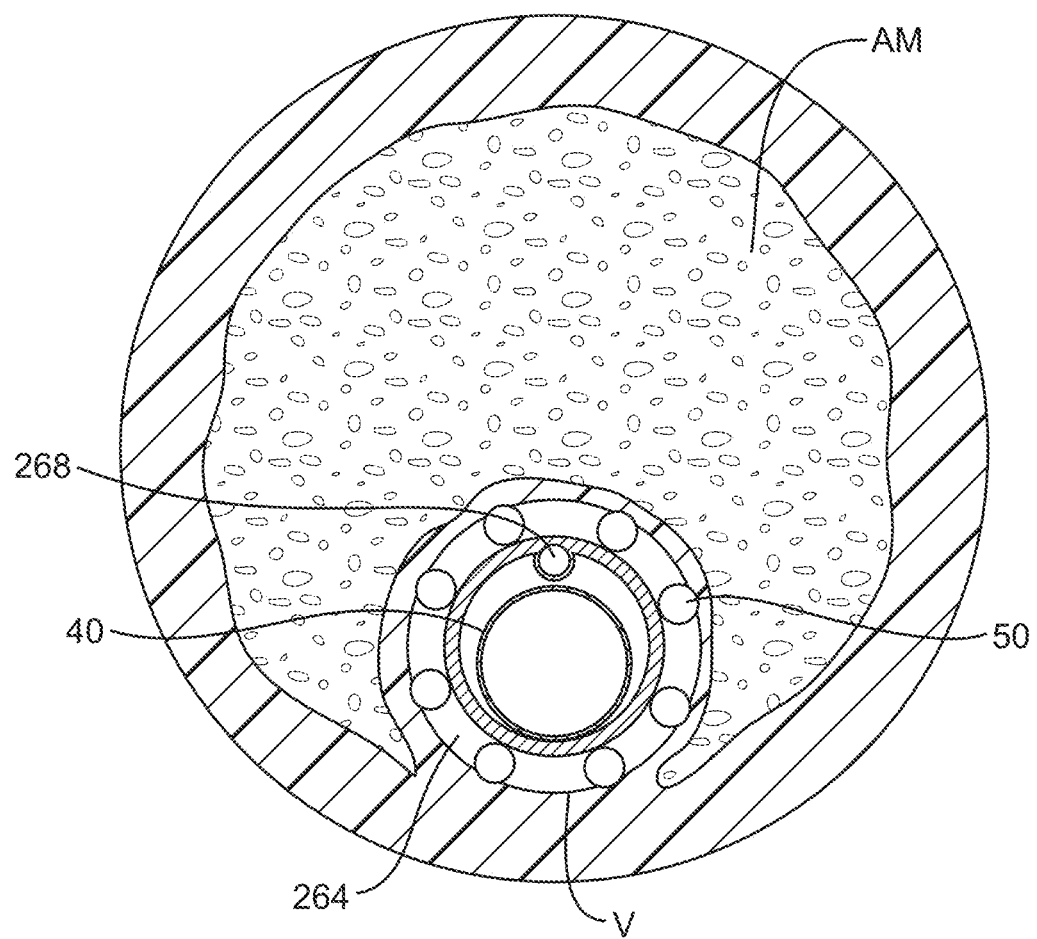
FIGS. 38F-38H are cross sectional views taken across a body lumen and treatment device to show additional aspects of the eccentric treatment methods and devices.
Figure 38G:
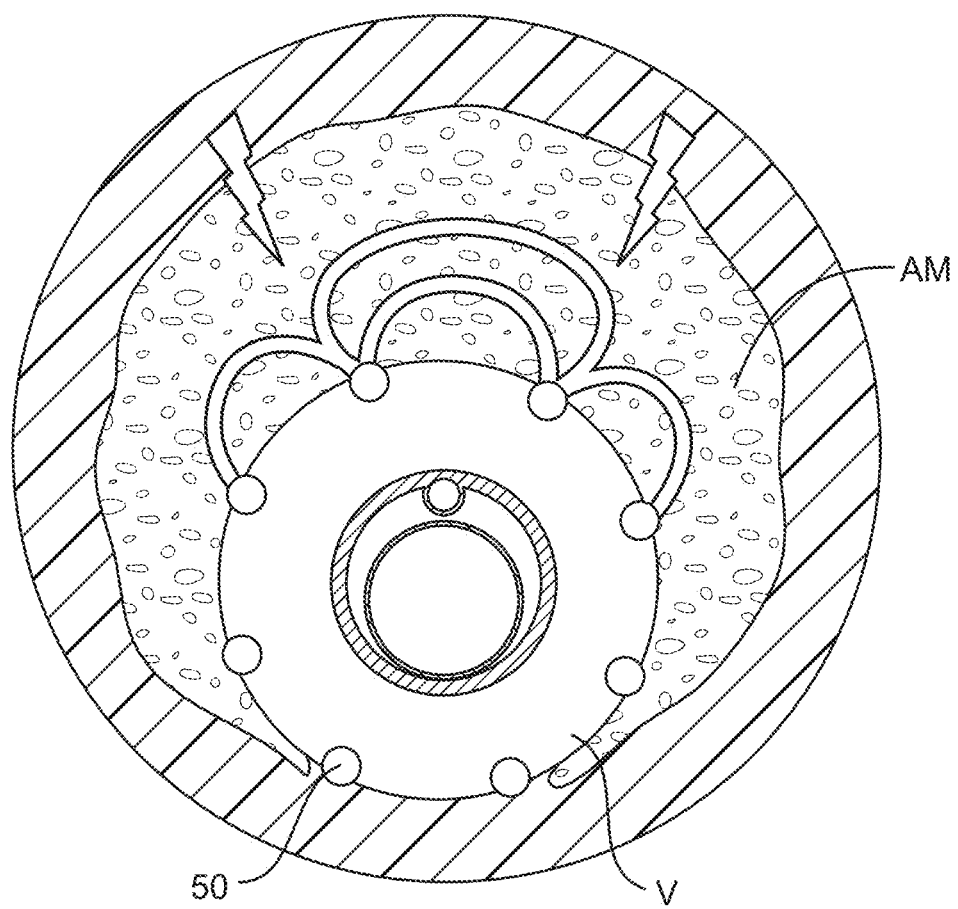
Figure 38H:
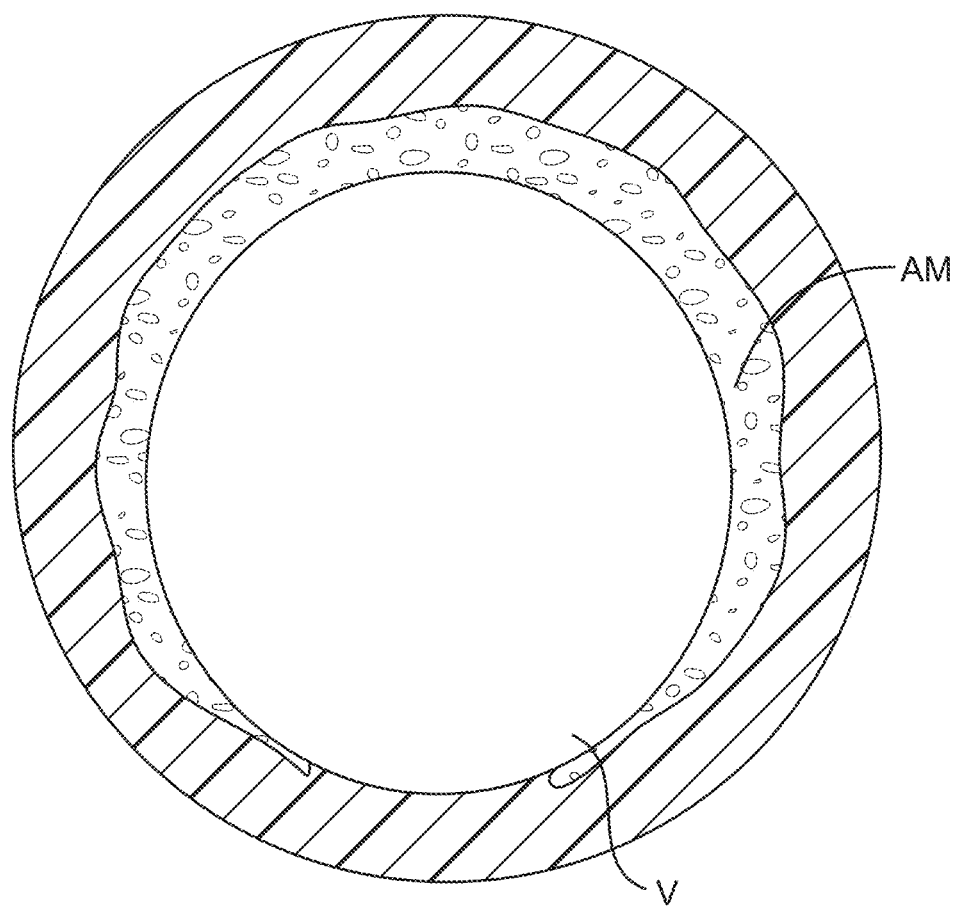
Figure 39A:
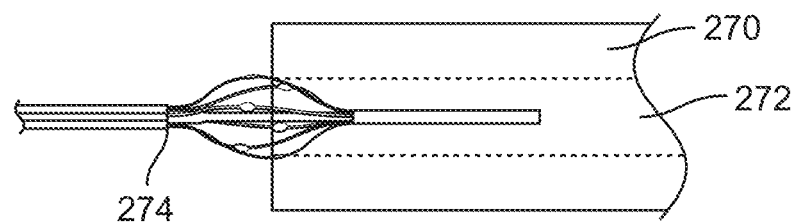
FIGS. 39A and 39B illustrate an eccentric treatment device and method in a gelatin artery model.
Figure 39B:
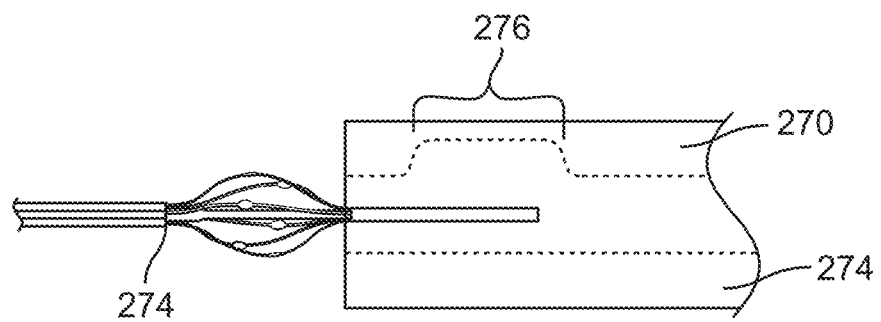

When the imaging catheter detects atherosclerotic material AM as illustrated in FIG. 38C, an appropriate subset (possibly including only a single electrode 50) is activated to remodel the atherosclerotic material AM, as illustrated in FIG. 38D, and the open vessel lumen size increases moderately during treatment. The catheter is pulled proximally to the next atheroma, which is again detected and treated. A cross section of the limited open lumen prior to treatment is schematically illustrated in FIG. 38F, which also illustrates a saline flush or irrigation lumen 268 of the catheter 264. Treatment energy and the moderate increase in the open lumen diameter of the vessel V are schematically illustrated in the cross section of FIG. 38G. After a healing response gradually increases the open lumen diameter, the longer term open lumen results schematically illustrated in FIG. 38H may then be provided.

Referring now to FIGS. 38A and B, eccentric material removal in a gelatin artery model 270 are presented. Prior to the test, the artery model includes a consistent lumen 272 as seen in FIG. 38A. A test eccentric treatment catheter 274 having an expandable basket supporting a circumferential array of electrodes is introduced into lumen 272, with the expandable basket supporting the electrodes in engagement with the luminal wall. Selected electrodes of test catheter 274 were energized so as to eccentrically treat the gelatin artery model 274, thereby effecting eccentric remodeling of the gelatin model, in this case by removing an eccentric volume 276 from along one side of lumen 272. The orientation and amount of the material removed was controlled by selectively energizing electrodes of test catheter 274.

Figure 40:
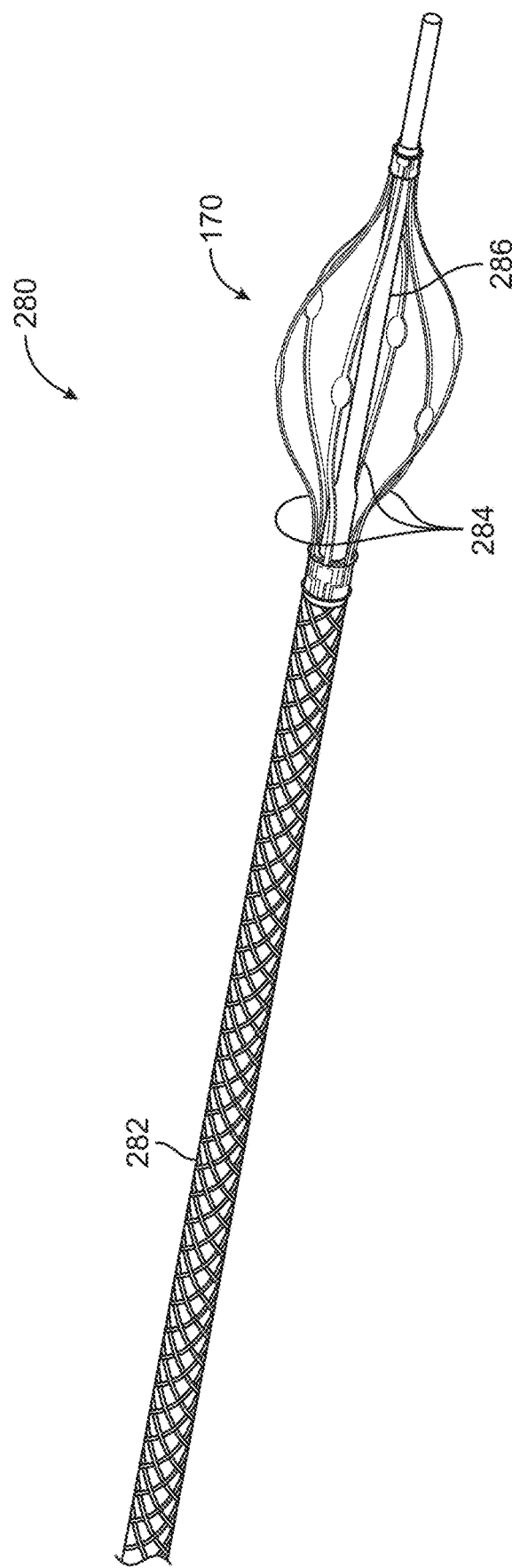
FIG. 40 is a perspective view of an exemplary catheter assembly.

Referring now to FIG. 40, an exemplary catheter system 280 is illustrated. In this embodiment, catheter body 282 includes only a single lumen, which is large enough to accommodate an imaging catheter therein and also to be used as an irrigation lumen to bring irrigation fluid to irrigation ports 284. The lumen may decrease in diameter distally of irrigation ports 284, with the decreased diameter portion 286 fittingly receiving the imaging catheter within the lumen thereof so as to direct the irrigation fluid radially outward through the plurality of irrigation ports. This embodiment may be particularly useful when remodeling atherosclerotic materials using the methods illustrated in FIGS. 38A-38H, in which mild heating improves vessel size without requiring aspiration.

Catheter body 282 may include a braided shaft in which conductive wires (for example copper wires or beryllium-copper wires) are coated with a high temperature and/or high strength insulation material such as a layer of polyimide or the like. The braided wires may be sandwiched between layers of materials forming the shaft of catheter body 282. The shaft may, for example, comprise a plurality of layers of polyethylene, an inner Teflon™ PTFE layer, an outer nylon layer, and the like.

The wires of shaft 282 may be braided so as to inhibit capacitive losses between wires when electrical currents run through them. Capacitive losses may be decreased when a wire that carries a current from an energy source to an electrode of the catheter system and a wire that carries a current from an electrode back to the energy source are not parallel, but at an angle, ideally being perpendicular. This may be achieved by braiding the wires with appropriate pitch or a number of peaks per inch. The basket structure 170 of catheter system 280 may be included, with the basket structure being described in more detail with reference to FIGS. 29A-29H. Guide 286 may extend through basket 170 and may comprise a material transparent to the imaging catheter, optionally comprising HDPE, PET, or the like.

Still further alternatives are available. For example, another way to employ RF energy to remodel atherosclerotic material may be to energize a plurality of the adjacent electrodes with differing RF signals so as to employ the adjacent electrodes as a phase-array. A phase array can direct or steer an electromagnetic signal in a desired direction using constructive and destructive interferences between signals of adjacent elements of the array. By controlling phases of the adjacent signals, a phase array of electrodes may provide a focused and/or steerable RF signal.

Along with controlling steering and directionality, adjusting phases of adjacent RF electrodes may allow focusing of some or most of the RF energy at a desired depth D inside the atherosclerotic material while inhibiting RF energy delivery between the electrode surfaces and depth D using constructive and destructive interference between the signals. For example, such a system may be employed to preserve the cap of a plaque so as to reduce restenosis. Inhibiting heating of the cap while focusing energy toward an internal portion of the plaque may lower an immune response to heat that could otherwise lead to restenosis. Hence, inhibiting heating of the cap may reduce restenosis.

In general, the present invention may use of highly elastic, expandable structures, particularly of expandable structures formed from structural members separated by perforations so as to define a "basket." Such structures can conform to an artery diameter before, during, and/or after atherosclerotic material removal. This expandability allows for direct contact of the electrodes against atheroma, although the systems of the present invention may also make use of conductive fluid environments to complete an RF energy path, or conversely, use non-conductive fluid to enhance energy directed through tissue. Multiple electrodes can be distributed circumferentially around an intermediate portion of the expandable structure, and a subset of these electrodes can be activated to allow for eccentric tissue remodeling and/or ablation.

Atheroma may be identified and targeted by intravascular imaging, and these capabilities may be integrated into the remodeling and/or ablation catheter. Preferably, the intravascular imaging capabilities will be deployed in a separate catheter which can be advanced within, and removed from the ablation catheter. In general, this intravascular imaging capability allows the progress of the therapy to be monitored so that wall perforation can be avoided, while ideally reducing occlusion to no more than 15% of the overall native vessel diameter (either upon completion of the treatment or after subsequent tissue healing). The ablation catheter may further allow the use of localized radiation or drug delivery for antirestenosis treatments. The ablation catheter may include a relatively large lumen allowing selective use of an intravascular imaging system, a radiation delivery or other treatment catheter, an aspiration of debris and vaporization gases, with these uses often being employed sequentially. A guidewire may make use of this or a separate lumen, and the guidewire may be removed to allow access for the restenosis and/or imaging catheters.

What is claimed is:

1. An apparatus, comprising:
   a catheter having a longitudinal axis and configured for placement within a body lumen of a human patient;
   an expandable member at a distal portion of the catheter configured to vary between a delivery configuration and a deployed configuration sized to fit within the body lumen of the human patient; and
   at least a first pair of bipolar contacts and a second pair of bipolar contacts disposed on the expandable member,
   wherein the first pair of bipolar contacts and the second pair of bipolar contacts are spaced apart lengthwise and angularly offset from one another relative to the longitudinal axis when the expandable member is in the deployed configuration,
   wherein each of the first pair of bipolar contacts and the second pair of bipolar contacts is configured to deliver thermal energy to less than a full circumference of the body lumen of the human patient,
   wherein the body lumen of the human patient is a blood vessel.

2. The apparatus of claim 1:
   wherein the first pair and the second pair of bipolar contacts are configured to deliver thermal energy to create respective first and second non-continuous, circumferential treatment zones along a lengthwise segment of the body lumen of the human patient; and
   wherein the first and the second non-continuous, circumferential treatment zones are formed in separate normal radial planes and are not continuous completely around the circumference of the body lumen of the human patient.

3. The apparatus of claim 2, wherein the first pair and the second pair of bipolar contacts are configured to respectively create the first and the second non-continuous, circumferential treatment zones in sequence.

4. The apparatus of claim 2, wherein the first pair and the second pair of bipolar contacts are configured to respectively create the first and the second non-continuous, circumferential treatment zones concurrently.

5. The apparatus of claim 1, further comprising:
   a third pair of bipolar contacts disposed on the expandable member; and
   a fourth pair of bipolar contacts disposed on the expandable member,
   wherein the third pair and fourth pairs of bipolar contacts are angularly offset from one another and from the first and the second pairs of bipolar contacts when the expandable member is in the deployed configuration,
   wherein each of the first, the second, the third and the fourth pairs of bipolar contacts are configured to deliver thermal energy to less than a full circumference of the body lumen of the human patient.

6. The apparatus of claim 1 wherein one or both of the first pair and the second pair of bipolar contacts further comprises at least one sensor configured to monitor a parameter of the apparatus or of a tissue of the body lumen of the human patient within the body lumen of the human patient.

7. The apparatus of claim 6, further comprising a feedback control system configured to alter treatment in response to the monitored parameter.

8. An apparatus, comprising:
   a catheter having a longitudinal axis and configured for placement within a body lumen of a human patient;
   an expandable member at a distal portion of the catheter, wherein the expandable member has a delivery configuration and a deployed configuration; and
   at least a first pair of bipolar contacts and a second pair of bipolar contacts attached to the expandable member and separated lengthwise and radially offset from one another about the longitudinal axis when the expandable member is in the deployed configuration,
   wherein each of the first pair of bipolar contacts and the second pair of bipolar contacts is configured to deliver thermal energy to less than a full circumference of the body lumen of the human patient,
   wherein the body lumen of the human patient is a blood vessel, and
   wherein the expandable member is configured to not block fluid flow within the body lumen of the human patient during energy delivery.

9. The apparatus of claim 8, wherein the first pair of bipolar contacts further comprises at least one sensor configured to monitor a parameter of the apparatus or of a tissue of the body lumen of the human patient within the human patient.

10. The apparatus of claim 9, further comprising a feedback control system configured to alter the delivery of thermal energy in response to the monitored parameter.

11. The apparatus of claim 8, wherein the catheter is configured for infusion of one or more agents into the body lumen of the human patient before, during, or after energy delivery.

12. A method of treatment a human patient using the apparatus of claim 1, comprising:
   inserting the catheter within the body lumen of the human patient;
   expanding the expandable member into contact with the body lumen of the human patient in the deployed configuration; and
   delivering thermal energy from each of the first pair and the second pair of bipolar contacts to less than a full circumference of the body lumen of the human patient.

13. The method of claim 12, further comprising:
   delivering thermal energy from each of the first pair and the second pair of bipolar contacts to create respective first and second non-continuous, circumferential treatment zones along a lengthwise segment of the body lumen of the human patient; and
   forming the first and the second non-continuous, circumferential treatment zones in separate normal radial planes that are not continuous completely around the circumference of the body lumen of the human patient.

14. The method of claim 13, further comprising creating the first and the second non-continuous, circumferential treatment zones in sequence.

15. The method of claim 13, further comprising creating the first and the second non-continuous, circumferential treatment zones concurrently.

16. The method of claim 12, wherein one or both of the first pair and the second pair of bipolar contacts further comprises at least one sensor, and further comprising monitoring a parameter of the catheter or of a tissue within the body lumen of the human patient with the at least one sensor.

17. The method of claim 16, further comprising altering the delivery of thermal energy in response to the monitored parameter.

18. The method of claim 12, wherein the thermal energy delivered is sufficient to alter neural activity in neural fibers within a wall of, or in proximity to, the body lumen of the human patient.

* * * * *